US012797587B2

(12) United States Patent
Kojima et al.

(10) Patent No.: US 12,797,587 B2
(45) Date of Patent: Nov. 17, 2026

(54) BALLOON FOR BALLOON CATHETER

(71) Applicant: KANEKA CORPORATION, Osaka (JP)

(72) Inventors: Masahiro Kojima, Settsu (JP); Takahisa Hamabuchi, Osaka (JP)

(73) Assignee: KANEKA CORPORATION, Osaka (JP)

( * ) Notice: Subject to any disclaimer, the term of this patent is extended or adjusted under 35 U.S.C. 154(b) by 637 days.

(21) Appl. No.: 18/265,325

(22) PCT Filed: Oct. 20, 2021

(86) PCT No.: PCT/JP2021/038820
§ 371 (c)(1),
(2) Date: Jun. 5, 2023

(87) PCT Pub. No.: WO2022/137764
PCT Pub. Date: Jun. 30, 2022

(65) Prior Publication Data

US 2024/0050712 A1 Feb. 15, 2024

(30) Foreign Application Priority Data

Dec. 24, 2020 (JP) ................................ 2020-215754

(51) Int. Cl.
*A61M 25/10* (2013.01)

(52) U.S. Cl.
CPC .... *A61M 25/1002* (2013.01); *A61M 25/1027* (2013.01); *A61M 25/10* (2013.01);
(Continued)

(58) Field of Classification Search
CPC .............. A61M 25/10; A61M 25/1002; A61M 2025/1004; A61M 25/1027;
(Continued)

(56) References Cited

U.S. PATENT DOCUMENTS 6,129,706 A * 10/2000 Janacek ............ A61M 25/1029 604/103.08
2005/0137618 A1* 6/2005 Kunis ............... A61M 25/1038 606/192
(Continued)

FOREIGN PATENT DOCUMENTS

JP 2008-529740 A 8/2008
JP 2014-506140 A 3/2014
(Continued)

OTHER PUBLICATIONS

International Search Report (PCT/ISA/210) issued in PCT/JP2021/038820, dated Dec. 28, 2021.
(Continued)

*Primary Examiner* — Kami A Bosworth
*Assistant Examiner* — Avery Smale
(74) *Attorney, Agent, or Firm* — Birch, Stewart, Kolasch & Birch, LLP

(57) ABSTRACT

Provided is a balloon for a balloon catheter that can incise a stenosis obliquely or incise a stenosis widely in the deflated state. A balloon for a balloon catheter having a balloon body (20) and a protrusion part (60) having a tip part (61), and satisfying the following (1) and/or (2): (1) the tip part (61) of the distal tapered part (24) is located on a first direction ($C_1$) side and not on a second direction ($C_2$) side in the circumferential direction of the balloon body (20) with respect to a straight line ($L_d$) in the deflated state; (2) the tip part (61) of the proximal tapered part (22) is located on a first direction ($C_1$) side and not on a second direction ($C_2$) side in the circumferential direction of the balloon body (20) with respect to a straight line ($L_p$) in the deflated state.

9 Claims, 13 Drawing Sheets

(52) U.S. Cl.
CPC . *A61M 2025/1004* (2013.01); *A61M 25/1029* (2013.01); *A61M 2025/1086* (2013.01); *A61M 2025/109* (2013.01); *A61M 2025/1093* (2013.01)

(58) Field of Classification Search
CPC ............ A61M 25/1029; A61M 25/104; A61M 2025/1086; A61M 2025/109; A61M 2025/1093; A61M 2025/1043; A61M 2025/1084; A61F 9/258; A61B 2018/0022; A61B 2018/00285; A61B 17/12136; A61B 17/320725
See application file for complete search history.

(56) References Cited

U.S. PATENT DOCUMENTS

| | | | | |
|---|---|---|---|---|
| 2006/0182873 | A1 | 8/2006 | Klisch et al. | |
| 2006/0276820 | A1 | 12/2006 | Yamaguchi et al. | |
| 2008/0124495 | A1 * | 5/2008 | Horn | A61M 25/1029 264/526 |
| 2010/0121372 | A1 * | 5/2010 | Farnan | A61M 25/104 606/194 |
| 2011/0196296 | A1 * | 8/2011 | Rickert | A61M 25/1038 604/96.01 |
| 2012/0130407 | A1 | 5/2012 | Aggerholm et al. | |
| 2014/0324079 | A1 | 10/2014 | Silvestro | |
| 2016/0128718 | A1 | 5/2016 | Aggerholm et al. | |
| 2018/0028221 | A1 | 2/2018 | Silvestro | |
| 2020/0179660 | A1 | 6/2020 | Ogawa et al. | |
| 2021/0113820 | A1 | 4/2021 | Okamoto et al. | |
| 2021/0113821 | A1 | 4/2021 | Okamoto et al. | |
| 2022/0152361 | A1 | 5/2022 | Kojima et al. | |

FOREIGN PATENT DOCUMENTS

| | | | |
|---|---|---|---|
| JP | 2016-52452 | A | 4/2016 |
| JP | 2016-520369 | A | 7/2016 |
| JP | 2018-102353 | A | 7/2018 |
| KR | 10-2020-0020862 | A | 2/2020 |
| WO | WO 2004/101057 | A1 | 11/2004 |
| WO | WO 2020/012850 | A1 | 1/2020 |
| WO | WO 2020/012851 | A1 | 1/2020 |
| WO | WO 2020/195170 | A1 | 10/2020 |

OTHER PUBLICATIONS

Extended European Search Report for European Application No. 21909921.5, dated Oct. 15, 2024.

* cited by examiner

[FIG. 1]
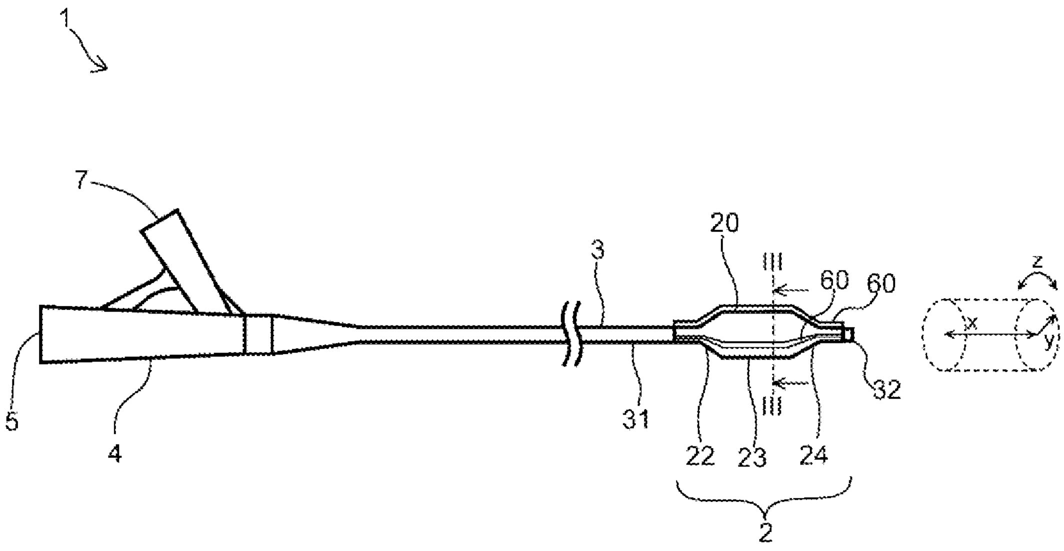
[FIG. 2]
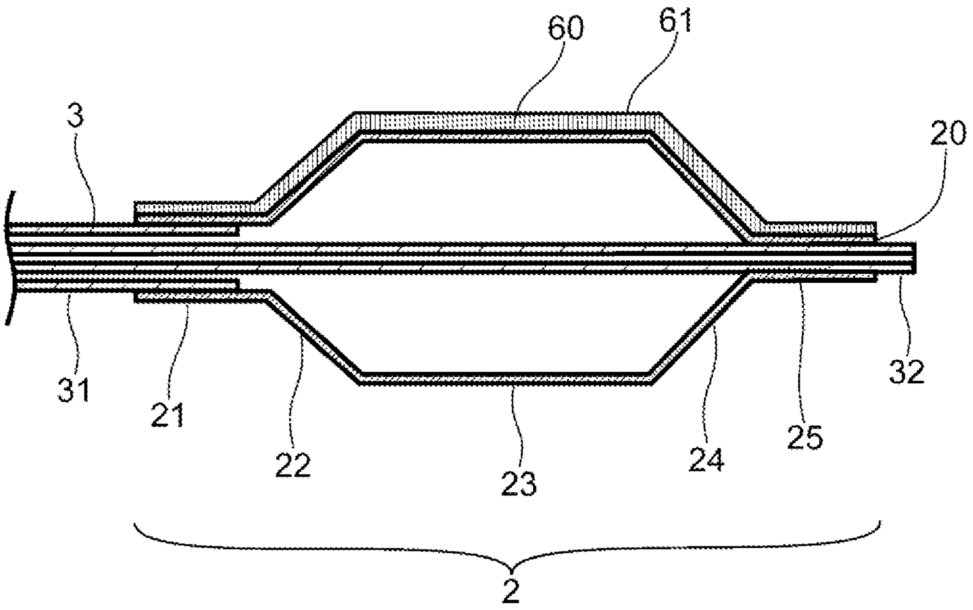

[FIG. 3]
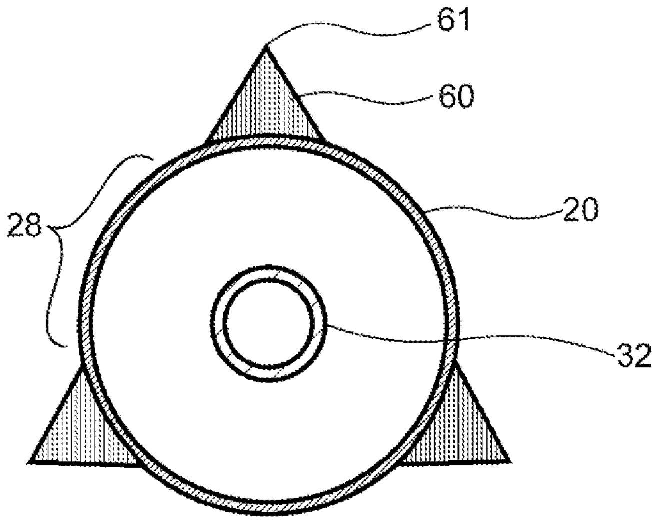
[FIG. 4]
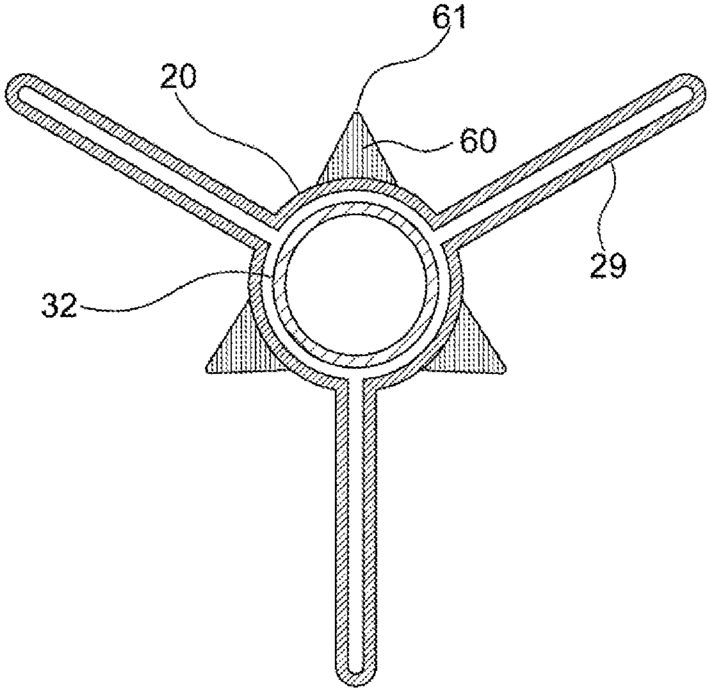

[FIG. 5]
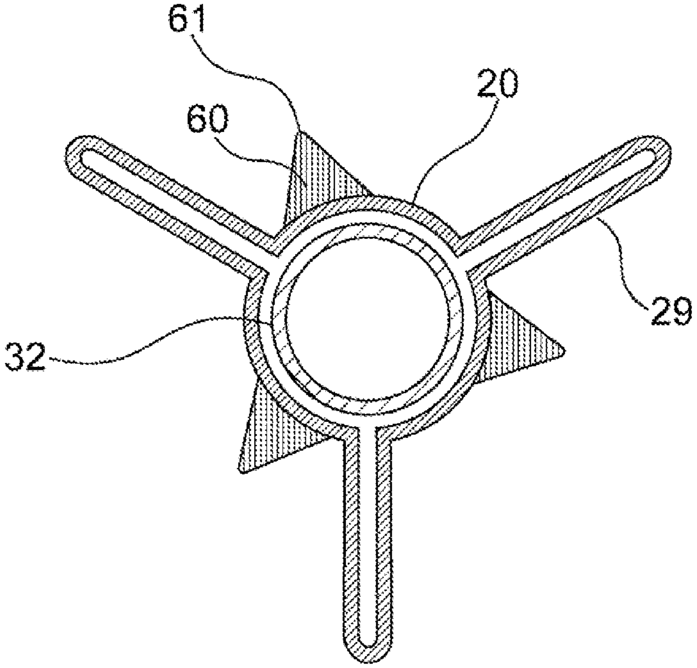
[FIG. 6]
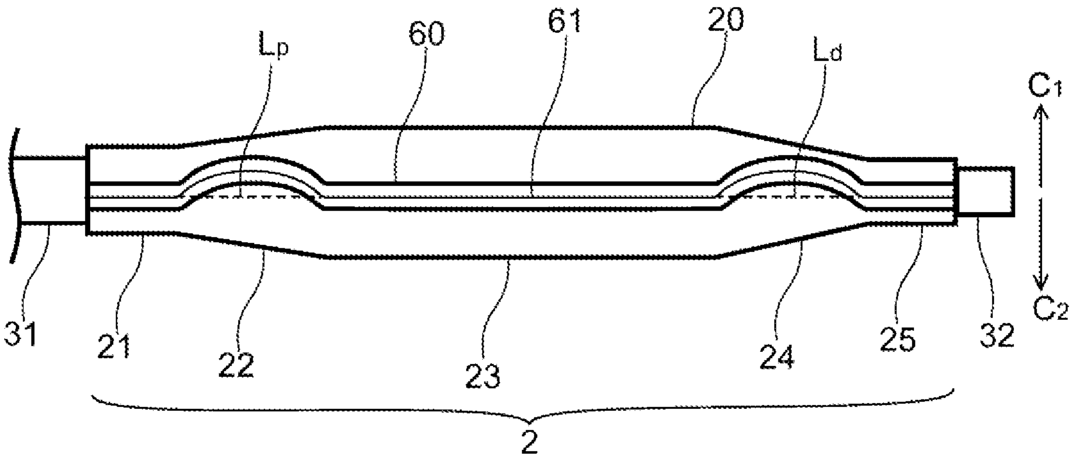

[FIG. 7]
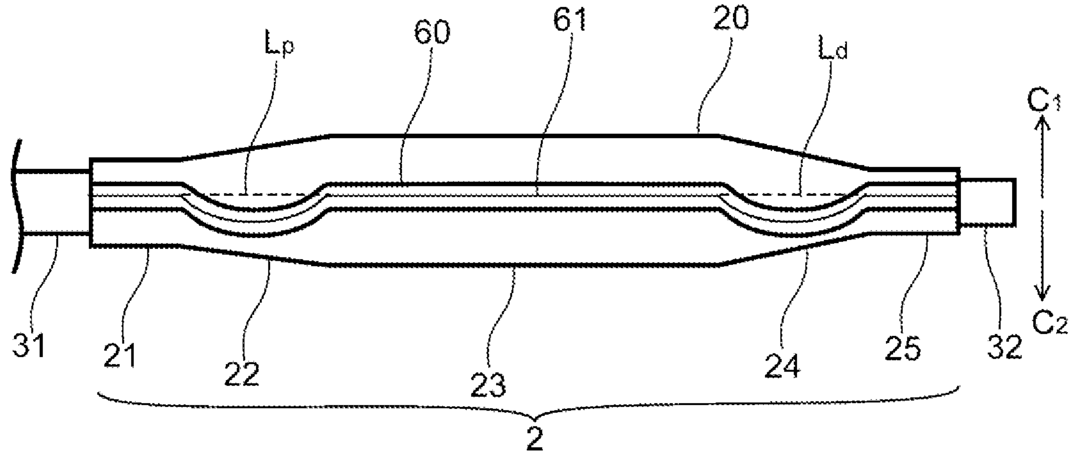
[FIG. 8]
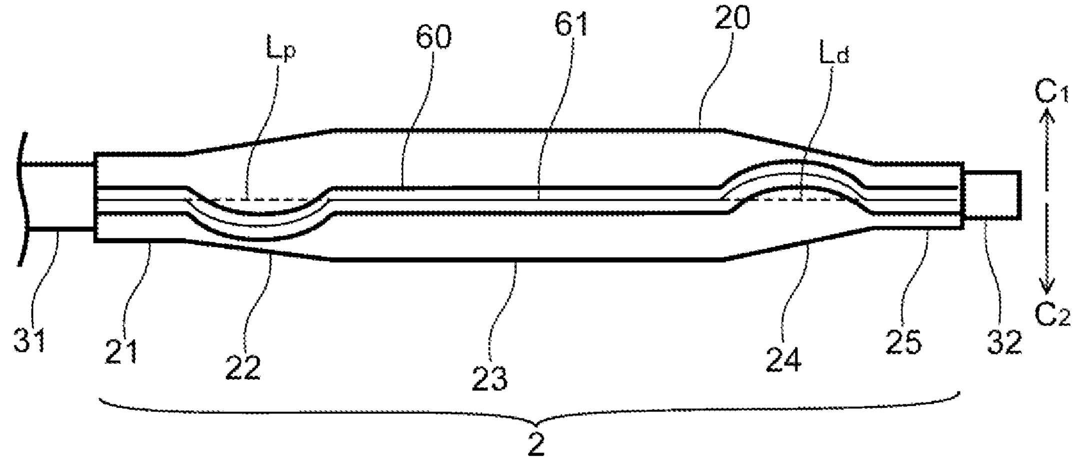
[FIG. 9]
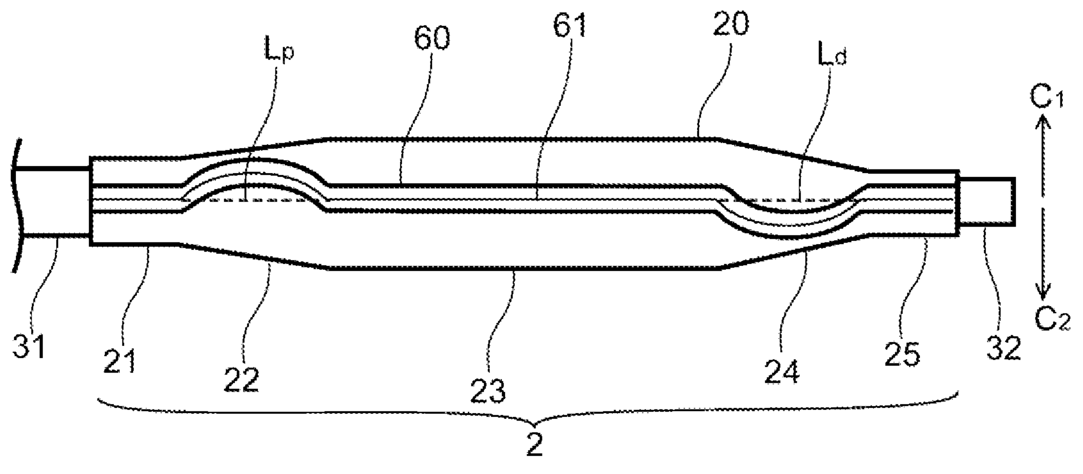

[FIG. 10]
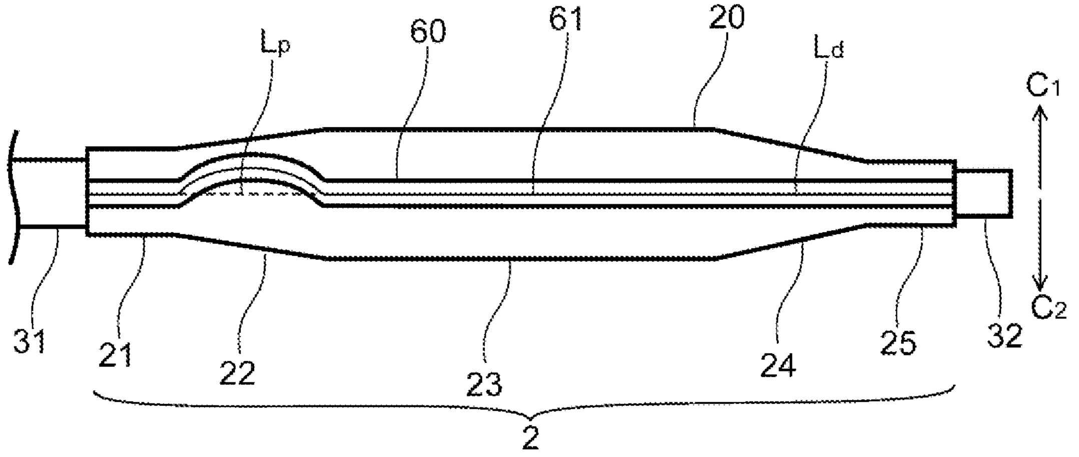
[FIG. 11]
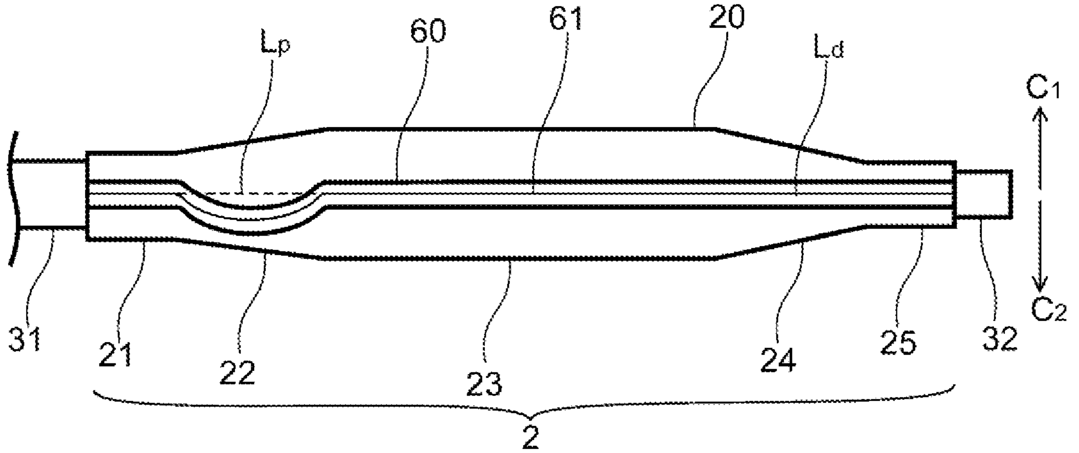
[FIG. 12]
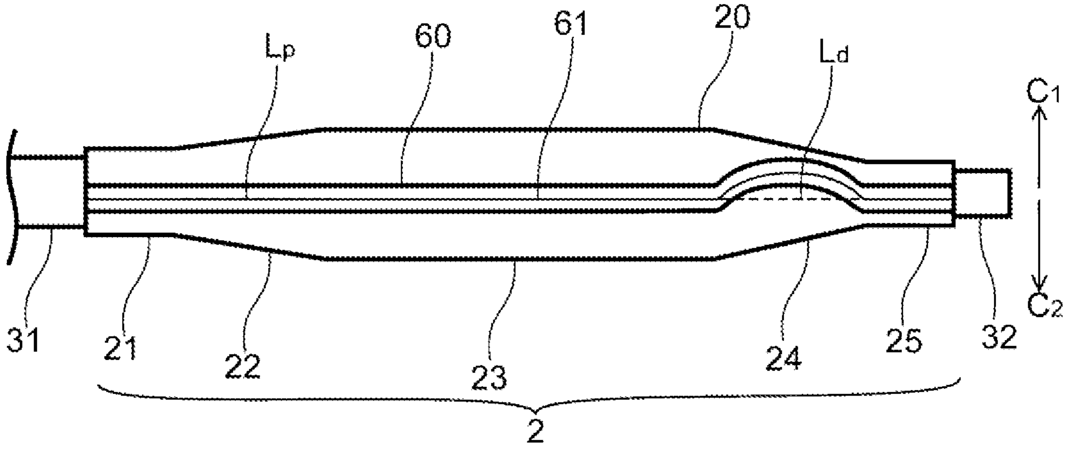

[FIG. 13]
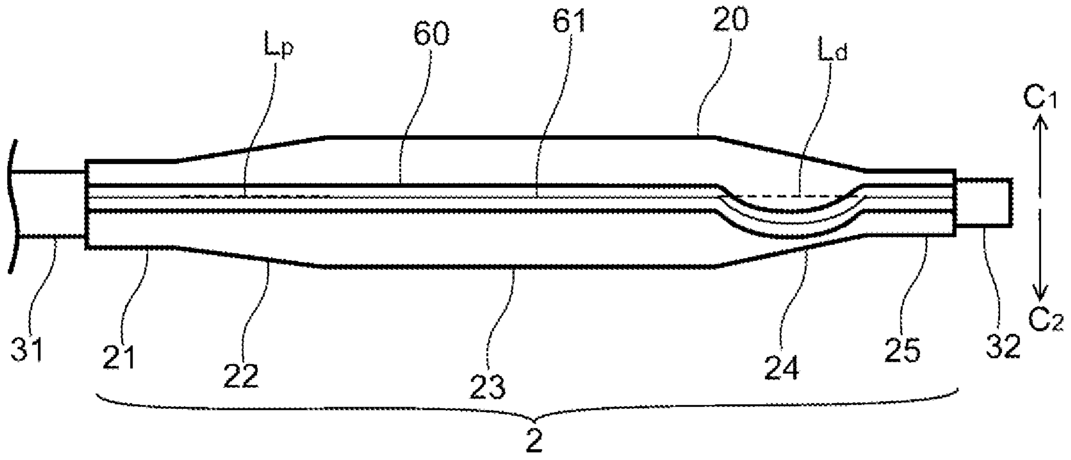
[FIG. 14]
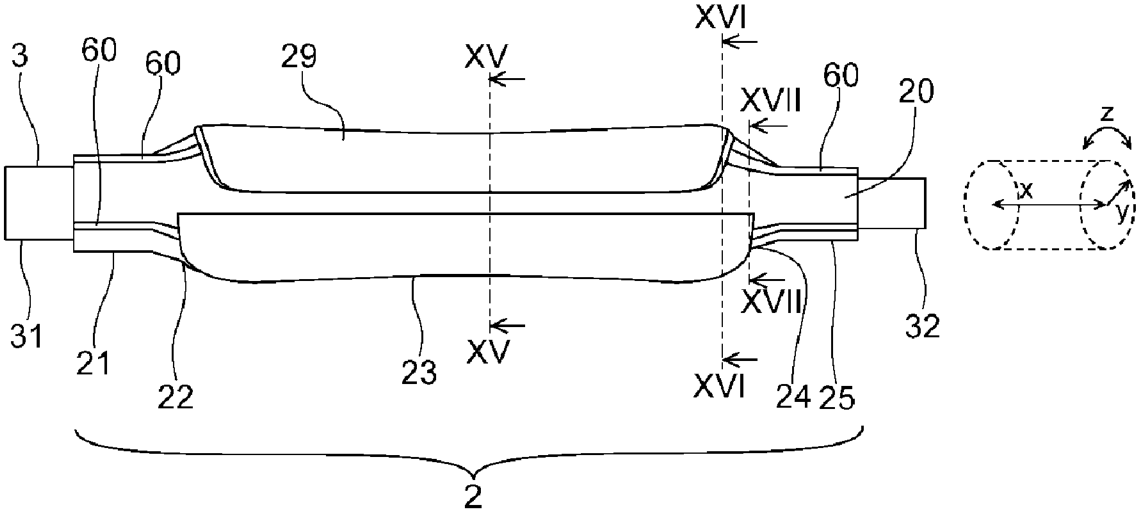

[FIG. 15]
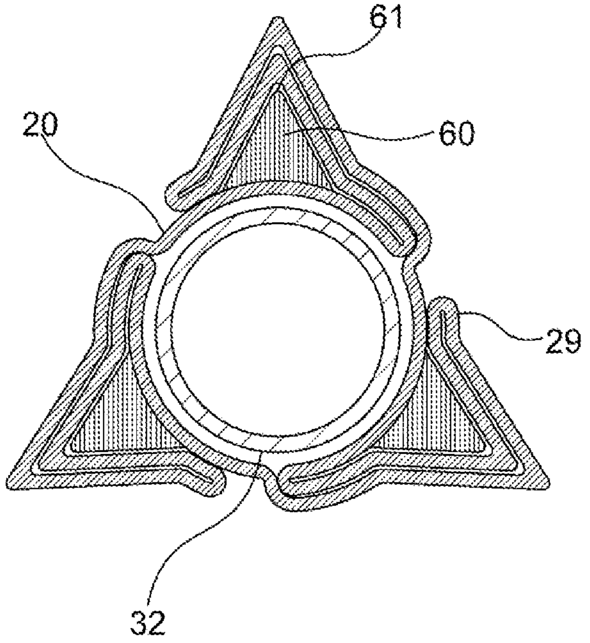
[FIG. 16]
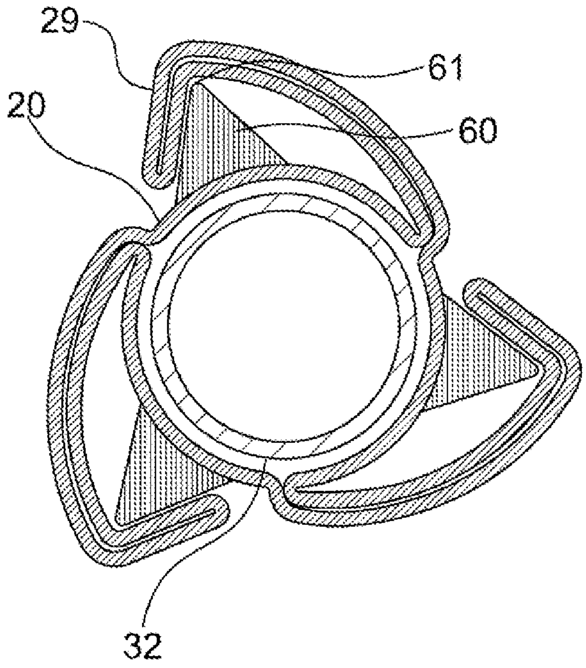

[FIG. 17]
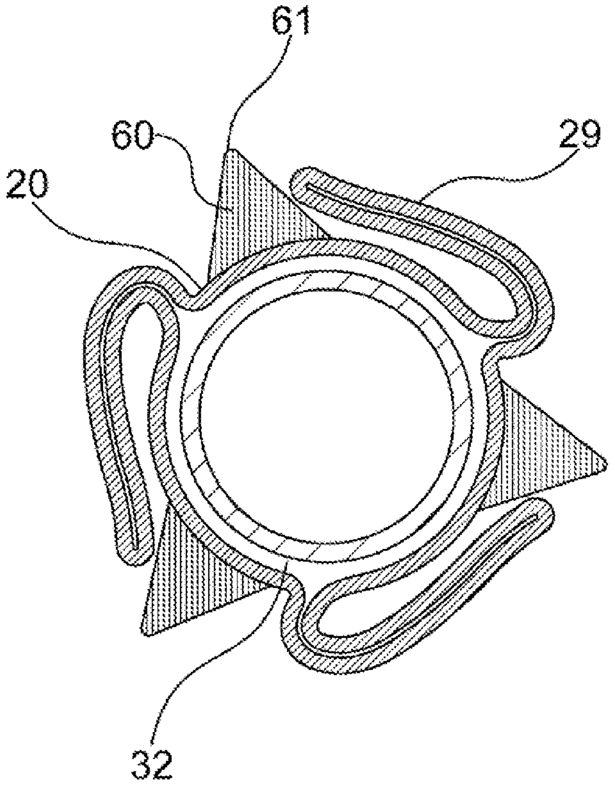
[FIG. 18]
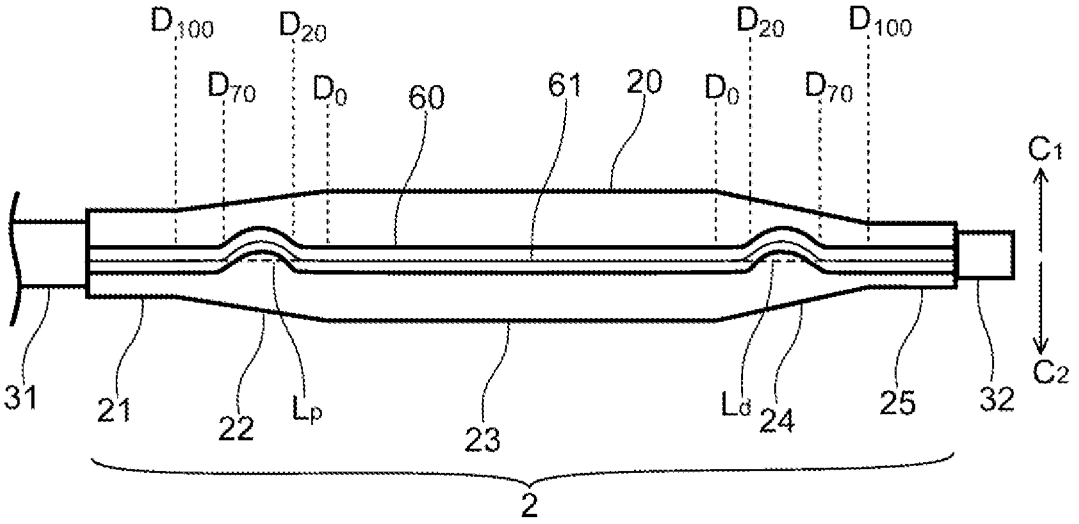

[FIG. 19]
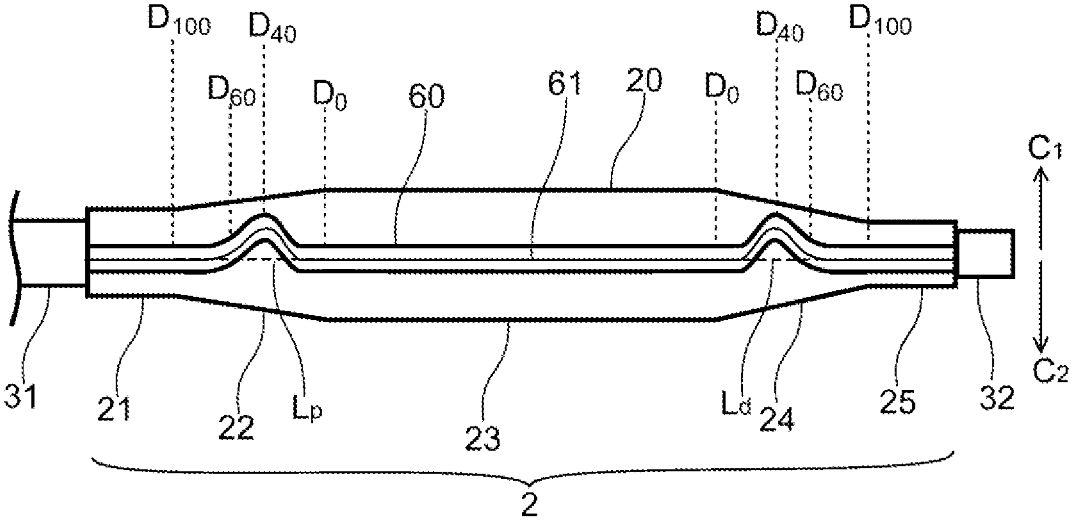
[FIG. 20]
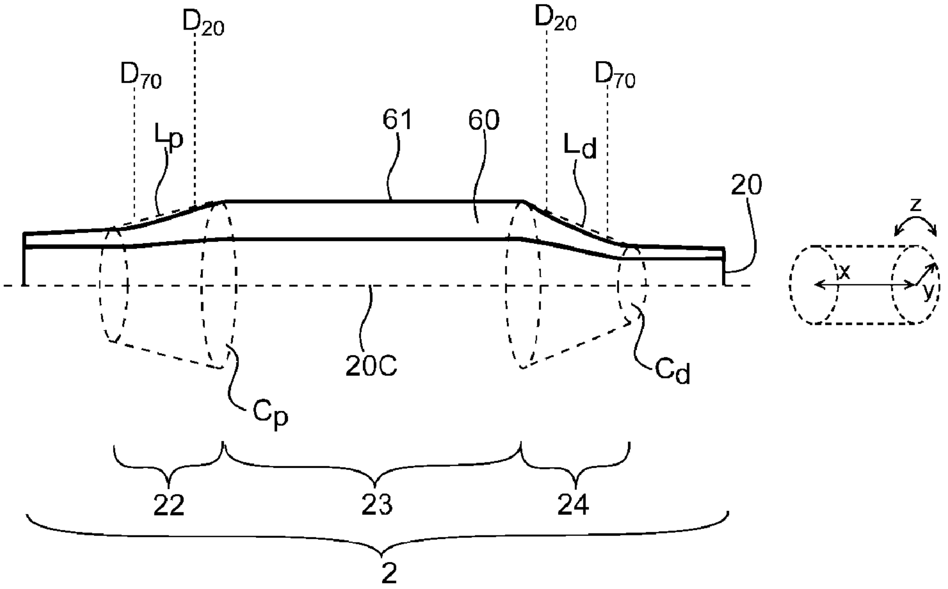

[FIG. 21]
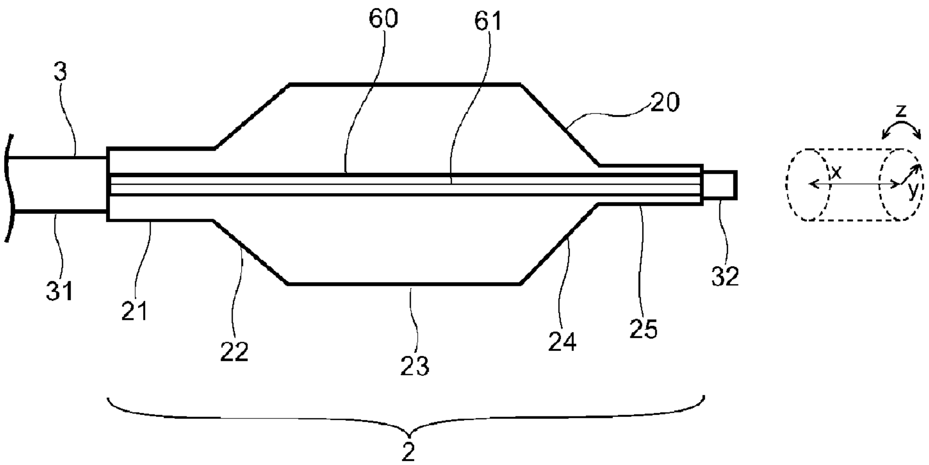
[FIG. 22]
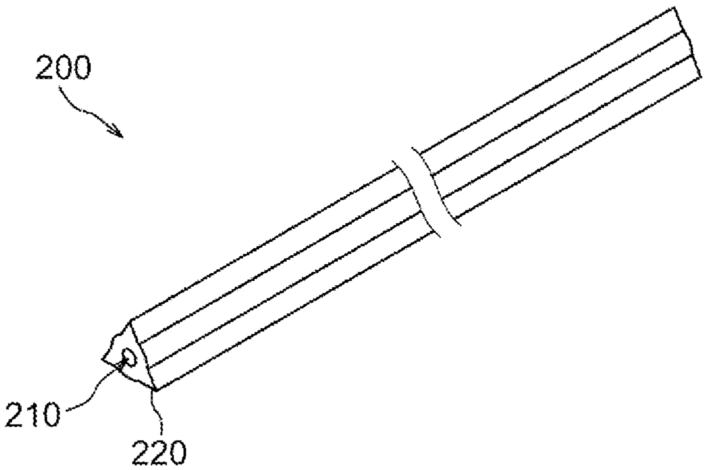

[FIG. 23]
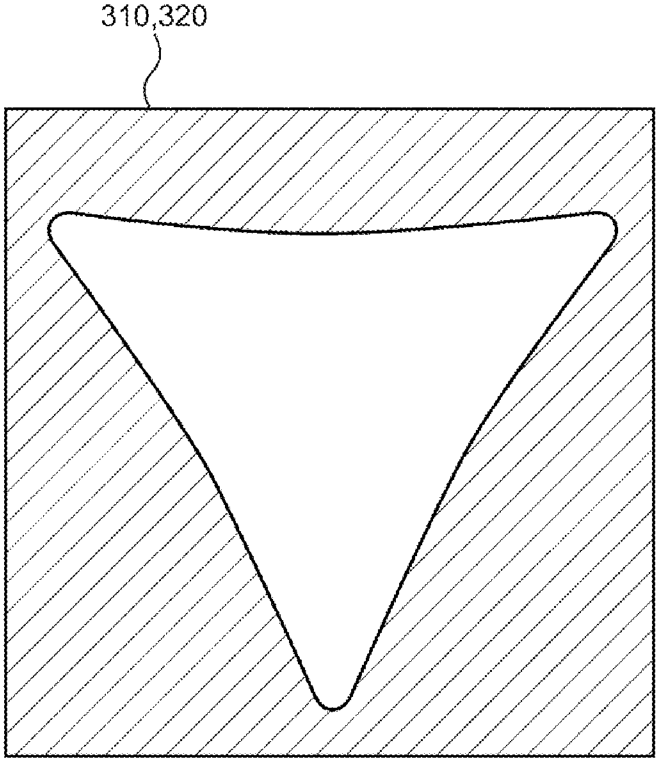
[FIG. 24]
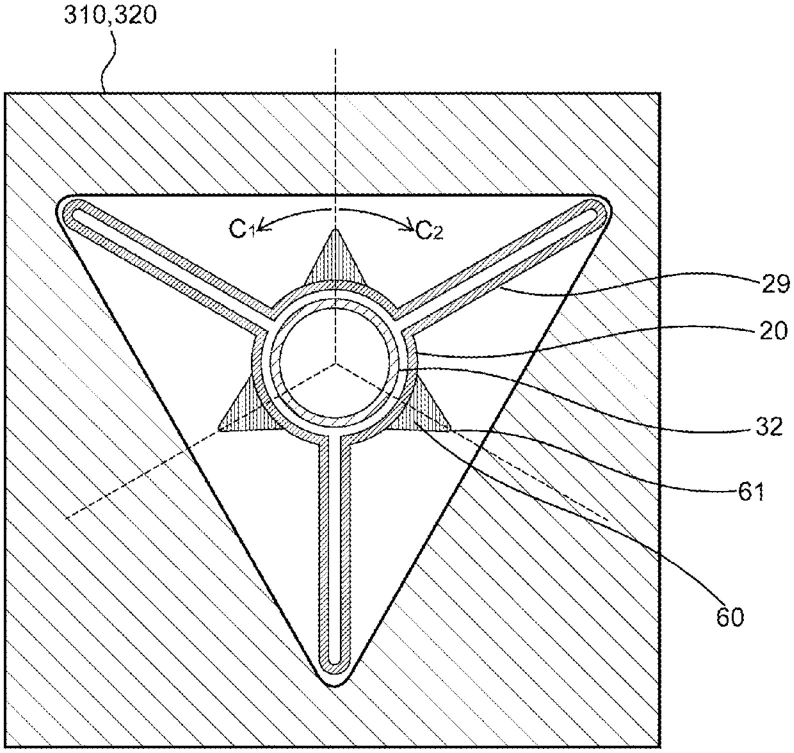

[FIG. 25]
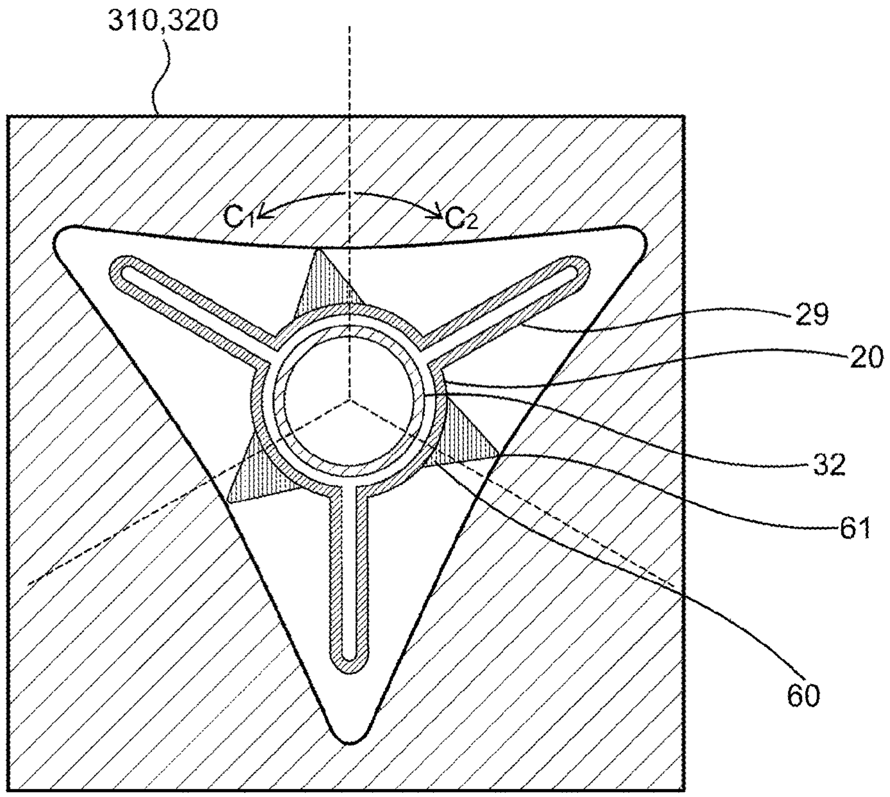
[FIG. 26]
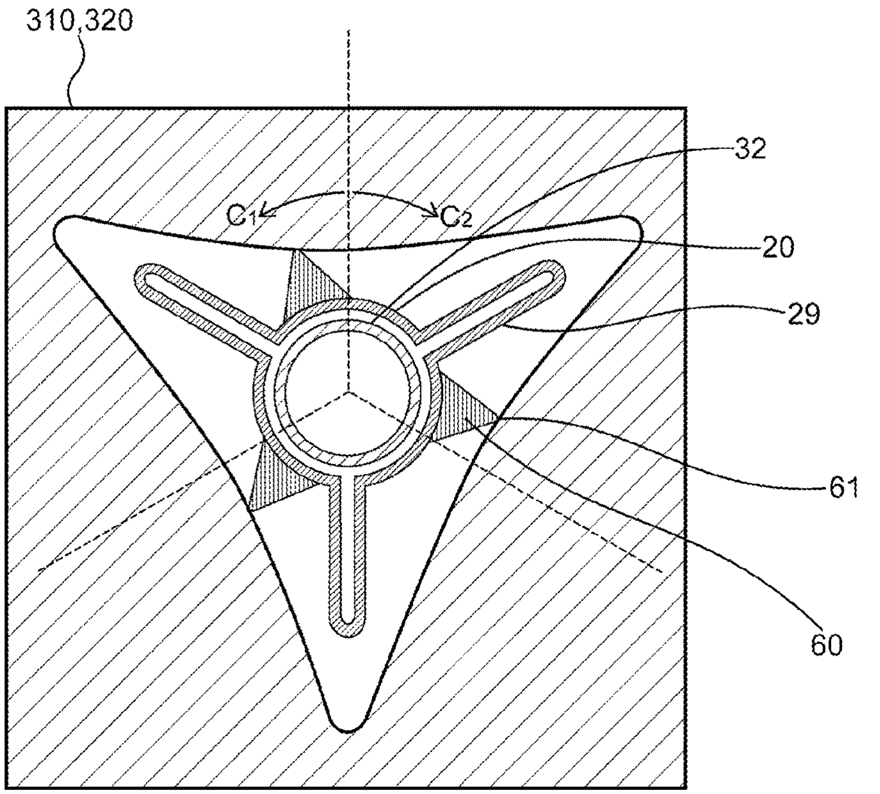

[FIG. 27]
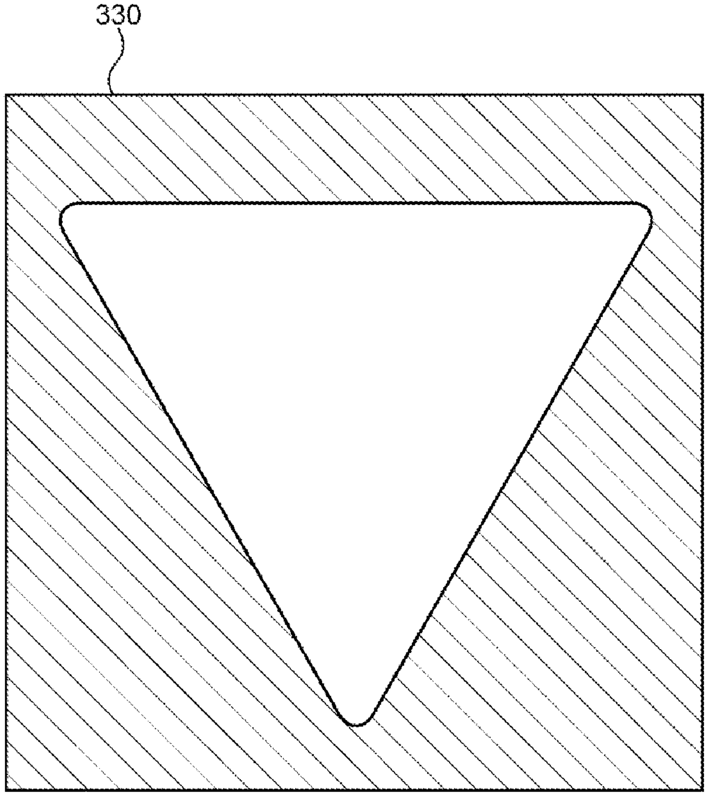

BALLOON FOR BALLOON CATHETER

TECHNICAL FIELD

The present invention relates to a balloon for a balloon catheter.

BACKGROUND ART

Diseases such as angina pectoris and myocardial infarction are caused by the formation of stenotic areas hardened by calcification and other factors in the inner walls of blood vessels. One of the treatments for these diseases is angioplasty, in which a balloon catheter is used to dilate the stenotic area. Angioplasty is a minimally invasive therapy that does not require an open chest procedure like bypass surgery and is widely used.

In angioplasty, it is sometimes difficult to dilate a stenosis that has hardened due to calcification and other factors with a standard balloon catheter. In some cases, while the method of dilating a stenosis by implanting an indwelling expansion device called a stent into the stenosis is also used, an ISR (In-Stent-Restenosis) lesion, for example, may occur after this treatment, in which the neointima of the vessel grows excessively and the vessel becomes stenotic again. The neointima in ISR lesions is soft and the surface is slippery, so a standard balloon catheter may cause the balloon to shift out of the lesion site during balloon dilation to damage the vessel.

Balloon catheters that can dilate a stenosis even in such calcified or ISR lesions include balloon catheters with a protrusion, blade, or scoring element on the balloon to bite into the stenosis. For example, Patent document 1 discloses a balloon catheter having a scoring element that is composed of a polymeric material stiffer than the polymeric material forming the balloon body, and that is flattened at one end and the other end of the balloon. Patent document 2 discloses a scoring balloon structure in which the height of the scoring element decreases along the tapered shape of the balloon, and Patent document 3 discloses a balloon catheter in which straight tubular part of the balloon has an outer protruding portion and the tapered part has an inner protruding portion. In the above Patent documents 1 to 3, the height of the scoring element decreases at ends of the balloon, or an inner protruding portion is provided instead of an outer protruding portion. On the other hand, there is a balloon catheter constructed such that the distal tapered part has a protruding portion higher than the protruding portion disposed at the straight tubular part of the balloon (Patent document 4).

RELATED ART DOCUMENT

Patent Document

Patent document 1: US 2016/0128718 A1
Patent document 2: JP 2014-506140 T
Patent document 3: WO2020/012851
Patent document 4: WO2020/012850

SUMMARY OF THE INVENTION

Problems to be Solved by the Invention

A balloon catheter is inserted into a body cavity in a deflated and folded state and delivered to the treatment site. For this reason, the balloon catheters disclosed in the above Patent documents 1 to 3 attempt to improve the passage of the balloon by decreasing the height of the scoring element at the end part of the balloon to prevent the outer diameter from becoming large so that the balloon can be easily inserted into a body cavity. In the balloon catheter disclosed in the above Patent document 4, since only the distal cone region is introduced into the lesion and the balloon is inflated, the height of the protruding portion disposed at the distal tapered part is high so that the balloon can be inflated while cutting into the lesion with the element disposed at the distal cone region. However, none of these balloons were designed to incise a stenosis obliquely or to incise a wide area in a single movement while the balloon is moved forward or backward in the deflated state.

In view of the above circumstances, the objective of the present invention is to provide a balloon for a balloon catheter that can incise a stenosis obliquely or incise a stenosis widely in the deflated state during balloon delivery or when the balloon is delivered to a lesion.

Means for Solving the Problems

A balloon for a balloon catheter in one embodiment of the present invention that can solve the above problem has a balloon body having an outer surface and an inner surface; the balloon body has a straight tubular part, a distal tapered part located distal to the straight tubular part, and a proximal tapered part located proximal to the straight tubular part; the distal tapered part, the straight tubular part, and the proximal tapered part have a protrusion part that projects outwardly in a radial direction from the outer surface of the balloon body and extends in a longitudinal axis direction of the balloon body; the protrusion part has a tip part in a cross section in the radial direction of the balloon body; and the balloon satisfies at least one of the following (1) and (2):

(1) in a deflated state of the balloon for a balloon catheter, the tip part of the protrusion part of the distal tapered part is located on a first direction side and not on a second direction side, or located on the second direction side and not on the first direction side, in a circumferential direction of the balloon body with respect to a straight line $L_d$ connecting the tip part at a proximal end of the distal tapered part and the tip part at a distal end of the distal tapered part; and (2) in a deflated state of the balloon for a balloon catheter, the tip part of the protrusion part of the proximal tapered part is located on a first direction side and not on a second direction side, or located on the second direction side and not on the first direction side, in a circumferential direction of the balloon body with respect to a straight line $L_p$ connecting the tip part at a distal end of the proximal tapered part and the tip part at a proximal end of the proximal tapered part.

Preferably, the balloon for a balloon catheter is folded in the deflated state of the balloon for a balloon catheter.

Preferably, when ends of the distal tapered part and the proximal tapered part on the straight tubular part side are termed as a position of 0% and the other ends of the distal tapered part and the proximal tapered part are termed as a position of 100% in the longitudinal axis direction of the balloon body in the deflated state of the balloon for a balloon catheter, the balloon satisfies at least one of the following (1) and (2):

(1) the tip part of the protrusion part in the entire extent of a section from a position of 20% to a position of 70% of the distal tapered part is located on the first direction side or on the second direction side with respect to the straight line $L_d$, and the tip part of the protrusion part in a section from a position of 90% to the position of 100% of the distal tapered part is not located on either the first direction side or the second direction side with respect to the straight line $L_d$; and (2) the tip part of the protrusion part in the entire extent of a section from a position of 20% to a position of 70% of the proximal tapered part is located on the first direction side or on the second direction side with respect to the straight line $L_p$, and the tip part of the protrusion part in a section from a position of 90% to the position of 100% of the proximal tapered part is not located on either the first direction side or the second direction side with respect to the straight line $L_p$.

In this case, the balloon preferably satisfies at least one of the following (1) and (2):

(1) a distance from the straight line $L_d$ to the tip part of the protrusion part at a position of 40% of the distal tapered part is 1.2 times or longer than a distance from the straight line $L_d$ to the tip part of the protrusion part at a position of 60% of the distal tapered part; and (2) a distance from the straight line $L_p$ to the tip part of the protrusion part at a position of 40% of the proximal tapered part is 1.2 times or longer than a distance from the straight line $L_p$ to the tip part of the protrusion part at a position of 60% of the proximal tapered part.

Preferably, the balloon satisfies at least one of the following (1) and (2) in the deflated state of the balloon for a balloon catheter:

(1) the tip part of the protrusion part in the entire extent of a section from a position of 20% to a position of 70% of the distal tapered part is located inside or at the same position in the radial direction of the balloon body with respect to an imaginary curved surface obtained by rotating the straight line $L_d$ around a central axis of the balloon body; and (2) the tip part of the protrusion part in the entire extent of a section from a position of 20% to a position of 70% of the proximal tapered part is located inside or at the same position in the radial direction of the balloon body with respect to an imaginary curved surface obtained by rotating the straight line $L_p$ around a central axis of the balloon body.

Preferably, the tip part of the protrusion part of the distal tapered part, the tip part of the protrusion part of the straight tubular part, and the tip part of the protrusion part of the proximal tapered part are located at the same position in the circumferential direction of the balloon body in an inflated state of the balloon for a balloon catheter.

Preferably, the balloon body has a wing forming portion that forms a wing in the deflated state, and the protrusion part is located outside the wing forming portion.

Preferably, the protrusion part of the distal tapered part, the protrusion part of the straight tubular part, and the protrusion part of the proximal tapered part extend continuously in the longitudinal axis direction of the balloon body.

Preferably, the protrusion part is composed of the same material as the balloon body.

The present invention also provides a method for producing the above-described balloon for a balloon catheter. A method in accordance with one embodiment of the present invention comprises: preparing a first tubular member, a second tubular member, and a third tubular member, each of which has an inner space extending in a longitudinal axis direction; preparing a balloon for a balloon catheter having a balloon body having an outer surface and an inner surface, the balloon body having a straight tubular part, a distal tapered part located distal to the straight tubular part, and a proximal tapered part located proximal to the straight tubular part, and the distal tapered part, the straight tubular part, and the proximal tapered part having a protrusion part that projects outwardly in a radial direction from the outer surface of the balloon body and extends in a longitudinal axis direction of the balloon body; and placing the distal tapered part in the first tubular member, placing the proximal tapered part in the second tubular member, and placing the straight tubular part in the third tubular member in the deflated state of the balloon for a balloon catheter, wherein the method satisfies at least one of the following (1) and (2):

(1) at least a part of the protrusion part of the distal tapered part is in contact with an inner surface of the first tubular member in the placing process; and (2) at least a part of the protrusion part of the proximal tapered part is in contact with an inner surface of the second tubular member in the placing process.

Effects of the Invention

The above balloon for a balloon catheter can incise a stenosis obliquely or incise a wide region while the balloon is moved forward or backward in the deflated state during balloon delivery or when the balloon is delivered to a lesion, because at least one of the tip part of the protrusion part of the distal tapered part and the proximal tapered part is located on the first direction side and not on the second direction side, or located on the second direction side and not on the first direction side, in the circumferential direction of the balloon.

BRIEF DESCRIPTION OF THE DRAWINGS

FIG. 1 is a side view of a balloon catheter in accordance with one embodiment of the present invention.

FIG. 2 is a cross-sectional view of the balloon of the balloon catheter shown in FIG. 1 in the inflated state in the longitudinal direction.

FIG. 3 is a III-III cross-sectional view of FIG. 1.

FIG. 4 is a cross-sectional view of the straight tubular part of the balloon shown in FIG. 2 in the deflated state in the radial direction.

FIG. 5 is a cross-sectional view of the tapered part of the balloon shown in FIG. 2 in the deflated state in the radial direction.

FIG. 6 is a plan view of the balloon shown in FIG. 2 in the deflated state seeing from the protrusion part side.

FIG. 7 is a plan view of a balloon in accordance with another embodiment of the present invention in the deflated state seeing from the protrusion part side.

FIG. 8 is a plan view of a balloon in accordance with still another embodiment of the present invention in the deflated state seeing from the protrusion part side.

FIG. 9 is a plan view of a balloon in accordance with still another embodiment of the present invention in the deflated state seeing from the protrusion part side.

FIG. 10 is a plan view of a balloon in accordance with still another embodiment of the present invention in the deflated state seeing from the protrusion part side.

FIG. 11 is a plan view of a balloon in accordance with still another embodiment of the present invention in the deflated state seeing from the protrusion part side.

FIG. 12 is a plan view of a balloon in accordance with still another embodiment of the present invention in the deflated state seeing from the protrusion part side.

FIG. 13 is a plan view of a balloon in accordance with still another embodiment of the present invention in the deflated state seeing from the protrusion part side.

FIG. 14 is a side view of the balloon shown in FIG. 2 in the folded state.

FIG. 15 is a XV-XV cross-sectional view of FIG. 14.

FIG. 16 is a XVI-XVI cross-sectional view of FIG. 14.

FIG. 17 is a XVII-XVII cross-sectional view of FIG. 14.

FIG. 18 is a plan view of a balloon in accordance with another embodiment of the present invention in the deflated state seeing from the protrusion part side.

FIG. 19 is a plan view of a balloon in accordance with still another embodiment of the present invention in the deflated state seeing from the protrusion part side.

FIG. 20 is a partial side view of the balloon shown in FIG. 2 in the deflated state.

FIG. 21 is a plan view of the balloon shown in FIG. 2 seeing from the protrusion part side.

FIG. 22 is a perspective view of a parison before expansion in accordance with one embodiment of the present invention.

FIG. 23 is a cross-sectional view perpendicular to the longitudinal axis direction of a first tubular member and a second tubular member of a producing method in accordance with one embodiment of the present invention.

FIG. 24 is a radial cross-sectional view in a process of placing the distal tapered part in the first tubular member or a process of placing the proximal tapered part in the second tubular member in the producing method in accordance with one embodiment of the present invention.

FIG. 25 is a radial cross-sectional view of the first tubular member or the second tubular member shown in FIG. 24 at different position in the longitudinal axis direction.

FIG. 26 is a radial cross-sectional view of the first tubular member or the second tubular member shown in FIG. 24 at still different position in the longitudinal axis direction.

FIG. 27 is a radial cross-sectional view of a third tubular member of the producing method in accordance with one embodiment of the present invention.

MODE FOR CARRYING OUT THE INVENTION

Hereinafter, the present invention will be described in detail based on the following embodiments, but the present invention is not limited by the following embodiments and can be altered in design within a scope in compliance with the intent described above and below, and all the changes are to be encompassed within a technical scope of the present invention. Note that, in each drawing, hatching, reference signs for components, and the like may be omitted for convenience of description, and in such a case, the specification and other drawings are to be referred to. Furthermore, since the dimensions of the various components in the drawings are provided for the purpose of facilitating the understanding of the feature of the present invention, the dimensions may differ from the actual dimensions in some cases.

A balloon for a balloon catheter in accordance with one embodiment of the present invention has a balloon body having an outer surface and an inner surface; the balloon body has a straight tubular part, distal tapered part located distal to the straight tubular part, and a proximal tapered part located proximal to the straight tubular part; the distal tapered part, the straight tubular part, and the proximal tapered part have a protrusion part that projects outwardly in a radial direction from the outer surface of the balloon body and extends in a longitudinal axis direction of the balloon body; the protrusion part has a tip part in a cross section in the radial direction of the balloon body; and the balloon satisfies at least one of the following (1) and (2):

(1) in a deflated state of the balloon for a balloon catheter, the tip part of the protrusion part of the distal tapered part is located on a first direction side and not on a second direction side, or located on the second direction side and not on the first direction side, in a circumferential direction of the balloon body with respect to a straight line $L_d$ connecting the tip part at a proximal end of the distal tapered part and the tip part at a distal end of the distal tapered part; and (2) in a deflated state of the balloon for a balloon catheter, the tip part of the protrusion part of the proximal tapered part is located on a first direction side and not on a second direction side, or located on the second direction side and not on the first direction side, in a circumferential direction of the balloon body with respect to a straight line $L_p$ connecting the tip part at a distal end of the proximal tapered part and the tip part at a proximal end of the proximal tapered part.

Because the tip part of the protrusion part of at least one of the distal tapered part and the proximal tapered part is located on the first direction side or the second direction side in the circumferential direction of the balloon body in the deflated state of the balloon, the balloon can incise a stenosis obliquely or incise a wide area in a single movement while the balloon is moved forward or backward in the deflated state. In the present specification, the balloon for a balloon catheter may be referred to simply as the "balloon".

Referring to FIG. 1 to FIG. 21, the balloon for a balloon catheter will be explained. FIG. 1 is a side view of a balloon catheter in accordance with one embodiment of the present invention, FIG. 2 is a cross-sectional view of the balloon of the balloon catheter shown in FIG. 1 in the inflated state in the longitudinal direction, and FIG. 3 is a III-III cross-sectional view of FIG. 1. FIG. 4 is a cross-sectional view of the straight tubular part of the balloon shown in FIG. 2 in the deflated state in the radial direction, and FIG. 5 is a cross-sectional view of the tapered part of the balloon shown in FIG. 2 in the deflated state in the radial direction. FIG. 6 is a plan view of the balloon shown in FIG. 2 in the deflated state seeing from the protrusion part side, and FIGS. 7 to 13 are plan views of a balloon in accordance with different embodiments of the present invention in the deflated state seeing from the protrusion part side. FIG. 14 is a side view of the balloon shown in FIG. 2 in the folded state, and FIG. 15, FIG. 16, and FIG. 17 is a XV-XV cross-sectional view, XVI-XVI cross-sectional view, and XVII-XVII cross-sectional view of FIG. 14, respectively. FIGS. 18 and 19 are plan views of a balloon in accordance with different embodiments of the present invention in the deflated state seeing from the protrusion part side. FIG. 20 is a partial side view of the balloon shown in FIG. 2 in the deflated state, that is, a view of a part in which a protrusion part is formed along the balloon body seeing from directly across. FIG. 21 is a plan view of the balloon shown in FIG. 2 seeing from the protrusion part side.

In the present invention, a proximal side refers to the direction towards a user's or operator's hand in the extending direction of a balloon catheter 1 or the longitudinal axis direction x of a shaft 3, and a distal side refers to the opposite side of the proximal side, that is, the direction towards the person to be treated. Members other than long-shaped members, such as the shaft 3, also has the same longitudinal axis direction x as the shaft 3. A radial direction y is the direction perpendicular to the longitudinal axis direction x, connecting the center of a balloon body 20 and a point on the circumscribed circle of the balloon body 20 in a cross section perpendicular to the longitudinal axis direction x. A circumferential direction z is the direction along the circumference of the circumscribed circle of the balloon body 20 in the inflated state in a cross section perpendicular to the longitudinal axis direction x.

As shown in FIGS. 1 and 2, a balloon catheter 1 has a shaft 3 and a balloon 2 disposed outside the shaft 3. The balloon catheter 1 has the distal side and the proximal side, and the balloon 2 is disposed on the distal side of the shaft 3. The balloon catheter 1 is configured such that fluid is introduced in the balloon 2 through the shaft 3, and the inflation and deflation of the balloon 2 can be controlled using an indeflator (pressurizer for balloons). The fluid may be a pressurized fluid pressurized by a pump or the like.

The shaft 3 preferably has a flow path for the fluid inside, and further has a guidewire insertion path. Configuration in which the shaft 3 has an internal fluid path and guidewire insertion path include, for example, a configuration in which the shaft 3 has an outer tube 31 and an inner tube 32, and the inner tube 32 serves as the guidewire insertion path and the space between the inner tube 32 and the outer tube 31 serves as the fluid flow path. In the case where the shaft 3 has the outer tube 31 and the inner tube 32, preferably, the inner tube 32 extends through the distal end of the outer tube 31 and penetrates the balloon 2 to the distal side, the distal side of the balloon 2 is fixed to the inner tube 32, and the proximal side of the balloon 2 is fixed to the outer tube 31.

As shown in FIGS. 1 to 13, the balloon 2 for a balloon catheter 1 has the balloon body 20 having an outer surface and inner surface; the balloon body 20 has a straight tubular part 23, a distal tapered part 24 located distal to the straight tubular part 23, and a proximal tapered part 22 located proximal to the straight tubular part 23; the distal tapered part 24, the straight tubular part 23, and the proximal tapered part 22 have a protrusion part 60 that projects outwardly in the radial direction from the outer surface of the balloon body 20 and extend in the longitudinal axis direction x; the protrusion part 60 has a tip part 61 in a cross section in the radial direction y of the balloon body 20; and the balloon 2 satisfies at least one of the following (1) and (2):

(1) in a deflated state of the balloon 2 for the balloon catheter 1, the tip part 61 of the protrusion part 60 of the distal tapered part 24 is located on a first direction $C_1$ side and not on a second direction $C_2$ side, or located on the second direction $C_2$ side and not on the first direction $C_1$ side, in a circumferential direction z of the balloon body 20 with respect to a straight line $L_d$ connecting the tip part 61 at a proximal end of the distal tapered part 24 and the tip part 61 at a distal end of the distal tapered part 24; and (2) in a deflated state of the balloon 2 for a balloon catheter 1, the tip part 61 of the protrusion part 60 of the proximal tapered part 22 is located on a first direction $C_1$ side and not on a second direction $C_2$ side, or located on the second direction $C_2$ side and not on the first direction $C_1$ side, in a circumferential direction z of the balloon body 20 with respect to a straight line $L_p$ connecting the tip part 61 at a distal end of the proximal tapered part 22 and the tip part 61 at a proximal end of the proximal tapered part 22.

In the deflated state of the balloon 2, the tip part 61 of the protrusion part 60 in at least one of the distal tapered part 24 and the proximal tapered part 22 is located on the first direction $C_1$ side or the second direction $C_2$ side in the circumferential direction z of the balloon body 20, and therefore, it is possible to incise the stenosis obliquely or incise a wide area with a single movement while moving the balloon 2 forward or backward in the deflated state during delivery of the balloon 2 or when the balloon 2 is delivered to the lesion.

As shown in FIG. 2, the balloon 2 may have a distal sleeve part 25 and a proximal sleeve part 21, which are non-inflatable, on the side distal to the distal tapered part 24 and proximal to the proximal tapered part 22, respectively. The distal sleeve part 25 and the proximal sleeve part 21 can be at least partially fixed to the shaft 3. When the shaft 3 has the outer tube 31 and the inner tube 32, at least a part of the proximal sleeve part 21 can be fixed to the outer tube 31 and at least a part of the distal sleeve part 25 can be fixed to the inner tube 32.

The distal tapered part 24 and the proximal tapered part 22 are preferably formed so that the diameter decreases as it is away from the straight tubular part 23. When the balloon 2 is inflated at a stenosis, the balloon body 20 having the straight tubular part 23 having the largest diameter in the inflated state allows the straight tubular part 23 to make sufficient contact with the stenosis to facilitate dilation or incise of the stenosis. In addition, while a wing 29 is formed when the balloon 2 is deflated as described below, the balloon body 20 having the distal tapered part 24 and the proximal tapered part 22 whose outer diameter decrease as they move away from the straight tubular part 23 allows the protrusion part 60 to be exposed from the wing 29 of the balloon 2 at the distal tapered part 24 and the proximal tapered part 22 when the balloon 2 is deflated and the wing 29 is wrapped around the shaft 3, and the exposed protrusion part 60 can incise the stenosis even when the balloon 2 is deflated.

As shown in FIG. 2 and FIG. 3, the protrusion part 60 of the balloon 2 is a part that projects outwardly in the radial direction y from the outer surface of the balloon body 20 in the inflated state of the balloon 2. The maximum length of the protrusion part 60 projecting outwardly in the radial direction y from the outer surface of the balloon body 20 in a cross section in the radial direction y is preferably 1.2 times or more the film thickness of the balloon body 20, more preferably 1.5 times or more, even more preferably 2 times or more, and is acceptable to be 100 times or less, 50 times or less, 30 times or less, or 10 times or less. This makes it easier to make an incision of appropriate depth in the stenosis with the protrusion part 60 and facilitate incision. Such a protrusion part 60 also makes it possible to improve the strength of the balloon 2 and prevent overinflation of the balloon 2 when pressurized.

The number of the protrusion part 60 in the circumferential direction z of the balloon 2 may be one, or more than one as shown in FIG. 3. When the balloon 2 has a plurality of the protrusion part 60 in the circumferential direction z, each protrusion part 60 is preferably spaced apart from each other in the circumferential direction z, and more preferably equally spaced in the circumferential direction z. A plurality of the protrusion part 60, each of which is spaced apart, preferably equally spaced, allows the balloon 2 to be easily fixed and facilitates incision of the stenosis.

As shown in FIG. 3, the protrusion part 60 has the tip part 61 in a cross section in the radial direction y of the balloon body 20. The tip part 61 makes it easier to make an incision into the stenosis, thereby preventing dissection of the vascular intima to incise the stenosis. The tip part 61 is a part of the protrusion part 60, and the tip part 61 projects most outwardly in the radial direction y from the outer surface of the balloon body 20, and may have a shape with an acute angle as shown in FIG. 3, or may have a shape with an obtuse angle, a shape comprising a curve, or a flat shape. From the point of view of ease of incision, it is preferable to have a shape with an acute angle. The cross-sectional shape of the protrusion part 60 in the radial direction y may be any shape, and may be approximate triangle as shown in FIG. 3, or polygon, fan shape, wedge shape, convex shape, spindle shape, or the like.

As shown in FIG. 4 and FIG. 5, the deflated state of the balloon 2 is a state after fluid has been discharged from the inside of the balloon 2 or before fluid is introduced into the inside of the balloon 2. In the deflated state of the balloon 2, the wing 29 and a portion where the inner surface of the balloon body 20 is in close proximity to the shaft 3 are formed. In other words, as shown in FIG. 3, the balloon 2 in the inflated state has a wing forming portion 28 that is formed into the wing 29 in the deflated state. In the embodiments shown in FIG. 4 and FIG. 5, the shaft 3 has the outer tube 31 and the inner tube 32, and the balloon 2 has a portion where the inner surface of the balloon body 20 is in close proximity to the inner tube 32 in the deflated state. As can be understood by comparing FIG. 4, which shows a cross-sectional view of the straight tubular part 23 in the radial direction y in the deflated state, and FIG. 5, which shows a cross-sectional view of the tapered part (the distal tapered part 24 or the proximal tapered part 22) in the radial direction y in the deflated state, in a cross section in the radial direction y, the length of the wing 29 of the straight tubular part 23 in the radial direction y is longer than the length of the wing 29 of the tapered part in the radial direction y, because the straight tubular part 23 is a part having the largest diameter and the tapered part is a part having a reduced diameter in the inflated state. When the distal tapered part 24 and the proximal tapered part 22 are gradually reduced in diameter toward the distal and proximal sides, respectively, the length of the wing 29 in the radial direction y in a cross section in the radial direction y is also gradually reduced toward the distal and proximal sides, respectively, and the wing 29 may not by formed at a distal side part of the distal tapered part 24 and a proximal side part of the proximal tapered part 22. Preferably, the wing 29 is not formed at a distal end part of the distal tapered part 24 and a proximal end part of the proximal tapered part 22. When the wing 29 is not formed at the distal end part of the distal tapered part 24 and the proximal end part of the proximal tapered part 22, the protrusion part 60 can contact the body cavity wall without being impeded by the wing 29 at those parts, allowing the incision of the stenosis.

As shown in FIGS. 6 to 13, in the deflated state of the balloon 2, the tip part 61 of the protrusion part 60 in at least one of the distal tapered part 24 and the proximal tapered part 22 is, independently, located on the first direction $C_1$ side and not on the second direction $C_2$ side in the circumferential direction z of the balloon body 20 with respect to the straight line $L_d$ and the straight line $L_p$, respectively, or located on the second direction $C_2$ side and not on the first direction $C_1$ side. In other words, the tip part 61 of the protrusion part 60 in at least one of the distal tapered part 24 and the proximal tapered part 22 is not disposed on either side across the straight line $L_d$ and the straight line $L_p$. While FIGS. 6 to 13 show embodiments in which the tip part 61 of the protrusion part 60 in the entire extent from the distal end to the proximal end of at least one of the distal tapered part 24 and the proximal tapered part 22 is placed on the first direction $C_1$ side or the second direction $C_2$ side, the tip part 61 of the protrusion part 60 of at least one of the distal tapered part 24 and the proximal tapered part 22 only needs to have a part located on the first direction $C_1$ side or the second direction $C_2$ side, and the rest may be located on the straight line $L_d$ or the straight line $L_p$.

As shown in FIG. 6 and FIG. 7, the tip part 61 of the protrusion part 60 of both the distal tapered part 24 and the proximal tapered part 22 may be located on the first direction $C_1$ side or the second direction $C_2$ side with respect to the straight line $L_d$ and the straight line $L_p$. These configurations allow the tip part 61 of the protrusion part 60 at the distal tapered part 24 and the tip part 61 of the protrusion part 60 at the proximal tapered part 22 to be located on the same side of the circumferential direction z, allowing the tip part 61 to be located on the same side of the circumferential direction z when the balloon 2 is advanced or retracted in the body cavity. Thus, the same side of the body cavity wall in the circumferential direction z can be incised obliquely or a wide region can be incised with a single movement using the tip part 61 of the protrusion part 60 of both the distal tapered part 24 and the proximal tapered part 22.

As shown in FIG. 8 and FIG. 9, the tip part 61 of the protrusion part 60 of the distal tapered part 24 may be located on the first direction $C_1$ side or the second direction $C_2$ side with respect to the straight line $L_d$, and the tip part 61 of the protrusion part 60 of the proximal tapered part 22 may be located, contrary to the distal tapered part 24, on the second direction $C_2$ side or the first direction $C_1$ side with respect to the straight line $L_p$. These configurations allow the tip part 61 of the protrusion part 60 at the distal tapered part 24 and the tip part 61 of the protrusion part 60 at the proximal tapered part 22 to be located on different sides of the circumferential direction z, allowing the tip part 61 to be located on different sides of the circumferential direction z when the balloon 2 is advanced or retracted in the body cavity. Thus, different part of the body cavity wall can be incised obliquely depending on whether the balloon 2 moves forward or backward, or a wider region can be incised with a single movement.

As shown in FIG. 10 and FIG. 11, the tip part 61 of the protrusion part 60 of the proximal tapered part 22 may be located on the first direction $C_1$ side or the second direction $C_2$ side with respect to the straight line $L_p$, and the tip part 61 of the protrusion part 60 of the distal tapered part 24 may not be located on either the first direction $C_1$ side or the second direction $C_2$ side with respect to the straight line $L_d$. These configurations allow only the tip part 61 of the protrusion part 60 at the proximal tapered part 22 to be located on the first direction $C_1$ side or the second direction $C_2$ side in the circumferential direction z, and the tip part 61 of the protrusion part 60 of the distal tapered part 24 not to be curved in the circumferential direction z. Thus, the tip part 61 of the distal tapered part 24 can incise straightly, and the tip part 61 of the proximal tapered part 22 can incise obliquely of incise a wide region in a single movement while the balloon 2 is, for example, moved backward.

As shown in FIG. 12 and FIG. 13, the tip part 61 of the protrusion part 60 of the distal tapered part 24 may be located on the first direction $C_1$ side or the second direction $C_2$ side with respect to the straight line $L_d$, and the tip part 61 of the protrusion part 60 of the proximal tapered part 22 may not be located on either the first direction $C_1$ side or the second direction $C_2$ side with respect to the straight line $L_p$. These configurations allow only the tip part 61 of the protrusion part 60 at the distal tapered part 24 to be located on the first direction $C_1$ side or the second direction $C_2$ side in the circumferential direction z, and the tip part 61 of the protrusion part 60 of the proximal tapered part 22 not to be curved in the circumferential direction z. Thus, the tip part 61 of the proximal tapered part 22 can incise straightly, and the tip part 61 of the distal tapered part 24 can incise obliquely or incise a wide region in a single movement while the balloon 2 is, for example, moved forward.

As described above, the balloon 2 can be made most suitable for treating depending on a lesion to be treated by selecting various configurations as shown, for example, in FIGS. 6 to 13. While FIGS. 6 to 13 show the embodiments in which the straight line $L_d$ and the straight line $L_p$ extend in the longitudinal axis direction x, the straight line $L_d$ and the straight line $L_p$ may extend at an angle in the circumferential direction z with respect to the longitudinal axis direction x.

In addition, while FIGS. 6 to 13 show the embodiments in which the distal sleeve part 25 and the proximal sleeve part 21 also have the protrusion part 60, the distal sleeve part 25 and the proximal sleeve part 21 may not have the protrusion part 60, and may have an inner protrusion part that projects inwardly in the radial direction y from the inner surface of the balloon body 20. The distal sleeve part 25 and the proximal sleeve part 21 without the protrusion part 60 can make it easier for the balloon 2 to be inserted into the body cavity and moved forward or backward.

Regarding the length of the protrusion part 60 in the radial direction y in a cross section in the radial direction y, the length of the protrusion part 60 at the distal tapered part 24 and the proximal tapered part 22 is preferably shorter than the length of the protrusion part 60 at the straight tubular part 23. In addition, preferably, the tip part 61 of the protrusion part 60 at the distal tapered part 24 and the proximal tapered part 22 is not placed outward with respect to the straight line $L_d$ and $L_p$ in the inflated state. This can reduce the risk that the tip part 61 of the protrusion part 60 at the tapered parts other than the straight tubular part 23 acting on the lesion contacts a part that is not the target of treatment, such as a normal blood vessel, in the inflated state of the balloon 2.

As shown in FIGS. 14 to 17, the balloon 2 is preferably folded in the deflated state of the balloon 2. In the folded state of the balloon 2, the wing 29 formed by the deflation of the balloon 2 shown in FIG. 4 and FIG. 5 is wrapped around the shaft 3 in a circumferential manner. Since the straight tubular part 23 having the maximum diameter has the wing 29 the length of which in the radial direction y is long, the wrapping amount of the wing 29 is larger as shown in FIG. 15. On the other hand, in the distal tapered part 24 and the proximal tapered part 22 that have reduced diameter, the wing 29 has a shorter length in the radial direction y due to the reduced diameter, and in one embodiment of the present invention, the length is shorter toward the more distal and more proximal side. In one embodiment of the present invention, the wing 29 having shorter length at a part of the distal tapered part 24 and the proximal tapered part 22 close to the straight tubular part 23 than at the straight tubular part 23 is wrapped around the shaft 3 (inner tube 32) in a circumferential manner as shown in FIG. 16, and at a more distal or more proximal side, the wing 29 having still shorter length is wrapped around the shaft 3 (inner tube 32) in a circumferential manner as shown in FIG. 17. Alternatively, by adjusting the diameter of the balloon 2 or the number of the wing 29, the balloon 2 can be configured so that the wrapping amount of the wing 29 can be reduced even at a part of the distal tapered part 24 and the proximal tapered part 22 closer to the straight tubular part 23 as shown in FIG. 17, or even so that almost no wing 29 is formed. By folding the balloon 2, the balloon 2 can be easily inserted into the body cavity.

As shown in FIG. 18, in the deflated state of the balloon 2, ends of the distal tapered part 24 and the proximal tapered part 22 on the straight tubular part 23 side in the longitudinal axis direction x of the balloon body 20 are termed as a position of 0% $D_0$ and the other ends are termed as a position of 100% $D_{100}$, and the balloon 2 preferably satisfies the at least one of the following (1) and (2):

(1) the tip part 61 of the protrusion part 60 in the entire extent of a section from a position of 20% $D_{20}$ to a position of 70% $D_{70}$ of the distal tapered part 24 is located on the first direction $C_1$ side or on the second direction $C_2$ side with respect to the straight line $L_d$, and the tip part 61 of the protrusion part 60 in a section from a position of 90% $D_{90}$ to the position of 100% $D_{100}$ of the distal tapered part 24 is not located on either the first direction $C_1$ side or the second direction $C_2$ side with respect to the straight line $L_d$; and (2) the tip part 61 of the protrusion part 60 in the entire extent of a section from a position of 20% $D_{20}$ to a position of 70% $D_{70}$ of the proximal tapered part 22 is located on the first direction $C_1$ side or on the second direction $C_2$ side with respect to the straight line $L_p$, and the tip part 61 of the protrusion part 60 in a section from a position of 90% $D_{90}$ to the position of 100% $D_{100}$ of the proximal tapered part 22 is not located on either the first direction $C_1$ side or the second direction $C_2$ side with respect to the straight line $L_p$.

Since the section from the position of 90% $D_{90}$ to the position of 100% $D_{100}$ of the distal tapered part 24 and the proximal tapered part 22, which is farthest from the straight tapered part 23, is the tip side when the balloon 2 is moved forward or backward in the body cavity, straight incision into the body cavity wall with the tip side of the balloon 2 becomes available with the configuration in which the tip part 61 at the section of the protrusion part 60 in at least one of the distal tapered part 24 and the proximal tapered part 22 is not placed on either the first direction $C_1$ side or the second direction $C_2$ side with respect to the straight line $L_d$ or the straight line $L_p$. In addition to such a configuration, the configuration where the tip part 61 of the protrusion part 60 in the entire extent of a section from the position of 20% $D_{20}$ to the position of 70% $D_{70}$ of at least one of the distal tapered part 24 and the proximal tapered part 22 is located on the first direction $C_1$ side or on the second direction $C_2$ side with respect to the straight line $L_d$ or the straight line $L_p$ allows the straight incision that has been made with the tip side of the balloon 2 to be extended obliquely by moving the balloon 2 forward or backward, or can make an incision in wide area with a single movement.

While FIG. 18 shows the embodiment that satisfies both the above conditions (1) and (2), either the distal tapered part 24 or the proximal tapered part 22 may satisfy either the above condition (1) or (2). From the viewpoint of making a straight incision with both tip sides of the balloon 2, the distal tapered part 24 and the proximal tapered part 22 preferably satisfy both the above (1) and (2). This allows the tip sides of the balloon 2 to make a straight incision, whether the balloon 2 is moved forward or backward.

As shown in FIG. 19, the balloon 2 in accordance with embodiments of the present invention preferably further satisfies at least one of the following (1) and (2) in the above-described embodiment:

(1) the distance from the straight line $L_d$ to the tip part 61 of the protrusion part 60 at a position of 40% $D_{40}$ of the distal tapered part 24 is 1.2 times or longer than the distance from the straight line $L_d$ to the tip part 61 of the protrusion part 60 at a position of 60% $D_{60}$ of the distal tapered part 24; and (2) the distance from the straight line $L_p$ to the tip part 61 of the protrusion part 60 at a position of 40% $D_{40}$ of the proximal tapered part 22 is 1.2 times or longer than the distance from the straight line $L_p$ to the tip part 61 of the protrusion part 60 at a position of 60% $D_{60}$ of the proximal tapered part 22.

The distance from the straight line $L_d$ or the straight line $L_p$ to the tip part 61 of the protrusion part 60 at a position of 40% $D_{40}$ is preferably 1.5 times or longer than the distance from the straight line $L_d$ or the straight line $L_p$ to the tip part 61 of the protrusion part 60 at a position of 60% $D_{60}$, more preferably 2 times or longer. The distance from the straight line $L_d$ or the straight line $L_p$ to the tip part 61 of the protrusion part 60 at a position of 40% $D_{40}$ is preferably 10 times or shorter than the distance from the straight line $L_d$ or the straight line $L_p$ to the tip part 61 of the protrusion part 60 at a position of 60% $D_{60}$, more preferably 8 times or shorter, even more preferably 5 times or shorter. The above configuration allows the tip part 61 of the protrusion part 60 in at least one of the distal tapered part 24 and the proximal tapered part 22 to form more curved portion in the entire extent of the section from the position of 20% $D_{20}$ to the position of 70% $D_{70}$ in which the tip part 61 is located on the first direction $C_1$ side or the second direction $C_2$ side with respect to the straight line $L_d$ or the straight line $L_p$, thereby allowing an oblique incision while the balloon 2 is moved forward or backward, or incision of wide area in a single movement.

As shown in FIG. 20, the balloon 2 preferably satisfies at least one of the following (1) and (2) in the deflated state:

(1) the tip part 61 of the protrusion part 60 in the entire extent of the section from the position of 20% $D_{20}$ to the position of 70% $D_{70}$ of the distal tapered part 24 is located inside or at the same position in the radial direction y of the balloon body 20 with respect to an imaginary curved surface $C_d$ obtained by rotating the straight line $L_d$ around a central axis 20C of the balloon body 20; and (2) the tip part 61 of the protrusion part 60 in the entire extent of the section from the position of 20% $D_{20}$ to a position of 70% $D_{70}$ of the proximal tapered part 22 is located inside or at the same position in the radial direction y of the balloon body 20 with respect to an imaginary curved surface $C_p$ obtained by rotating the straight line $L_p$ around a central axis 20C of the balloon body 20.

This configuration where the tip part 61 of the protrusion part 60 of at least one of the distal tapered part 24 and the proximal tapered part 22 is located inside or at the same position in the radial direction y of the balloon body 20 with respect to the imaginary curved surface $C_d$ or the imaginary curved surface $C_p$ can reduce the diameter of the portion, allowing the balloon 2 to be easily inserted when moving forward or backward in the body cavity.

As shown in FIG. 20, the straight line $L_d$ and the straight line $L_p$ may be at an angle in the radial direction y with respect to the central axis 20C of the balloon body 20 (i.e., the longitudinal direction x). The imaginary curved surface $C_d$ and the imaginary curved surface $C_p$ in the embodiment where the straight line $L_d$ and the straight line $L_p$ are at an angle in the radial direction y with respect to the central axis 20C of the balloon body 20 are the side surface of a truncated cone, as shown in FIG. 20. When the diameter of the balloon 2 is large, or when the length of the protrusion part 60 at the straight tubular part 23 in the radial direction y is longer than the length of the protrusion part 60 at the distal tapered part 24 and the proximal tapered part 22 in the radial direction y in a cross section in the radial direction y, the straight line $L_d$ or the straight line $L_p$ is angled in the radial direction y with respect to the central axis 20C of the balloon body 20, and the imaginary curved surface $C_d$ and the imaginary curved surface $C_p$ are the side surface of a truncated cone the bottom surface of which is at the straight tubular part 23 side. In such an embodiment, the diameter of a distal side part and a proximal side part of the distal tapered part 24 and the proximal tapered part 22, respectively, can be kept small in the deflated state, and thus, the diameter of the portions that are tip sides when the balloon 2 is inserted into the body cavity and moved forward or backward is made small, allowing the balloon 2 to be easily inserted in the body cavity.

Although not shown in the figures, the straight line $L_d$ and the straight line $L_p$ may be parallel to the central axis 20C of the balloon body 20 (i.e., the longitudinal direction x). In the embodiment where the straight line $L_d$ and the straight line $L_p$ are parallel to the central axis 20C of the balloon body 20, the imaginary curved surface $C_d$ and the imaginary curved surface $C_p$ are the side surface of a cylinder. When the straight line $L_d$ and the straight line $L_p$ are parallel to the central axis 20C of the balloon body 20, the diameter of the straight tubular part 23 can be reduced in the deflated state of the balloon 2, and thus, the diameter of the straight tubular part 23 when the wing 29 formed by the deflation of the balloon 2 is wrapped around the shaft 3 also can be reduced, allowing easy insertion in the body cavity.

While FIG. 20 shows the embodiment where both the imaginary curved surface $C_d$ and the imaginary curved surface $C_p$ at the distal tapered part 24 and the proximal tapered part 22 are the side surface of a truncated cone, the imaginary curved surface $C_d$ at the distal tapered part 24 may be the side surface of a cylinder and the imaginary curved surface $C_p$ at the proximal tapered part 22 may be the side surface of a truncated cone, or vice versa.

While FIG. 20 shows the embodiment where both tapered parts in the entire extent of the section from the position of 20% $D_{20}$ to the position of 70% $D_{70}$ satisfy the above requirements (1) and (2), embodiments of the balloon 2 of the present invention include an embodiment where either the distal tapered part 24 or the proximal tapered part 22 satisfies the above requirement (1) or (2). From a viewpoint of improving insertion when the balloon 2 is inserted into the body cavity and moved forward to the lesion, the tip part 61 of the protrusion part 60 in the entire extent of the section from the position of 20% $D_{20}$ to the position of 70% $D_{70}$ of the distal tapered part 24 preferably placed inside or at the same position in the radial direction y of the balloon body 20 with respect to the imaginary curved surface $C_d$. This can make the diameter of the part that is at tip end side when the balloon 2 is inserted into the body cavity and moved forward small, allowing the balloon 2 to be more easily inserted in the body cavity.

As described above, in the embodiments of the balloon 2 of the present invention, the tip part 61 of the protrusion part 60 of at least one of the distal tapered part 24 and the proximal tapered part 22 is arranged curved on the first direction $C_1$ side or the second direction $C_2$ side in the circumferential direction z of the balloon body 20 independently with respect to the straight line $L_d$ and the straight line $L_p$, respectively in the deflated state of the balloon 2, but as shown in FIG. 21, in the inflated state, the tip part 61 of the protrusion part 60 of the distal tapered part 24, the tip part 61 of the protrusion part 60 of the straight tubular part 23, and the tip part 61 of the protrusion part 60 of the proximal tapered part 22 preferably located at the same position in the circumferential direction z of the balloon body 20. This allows the balloon 2 to be capable of making a straight incision when the balloon is inflated at a lesion or the like after delivery, and in the deflated state, the balloon can make an oblique incision by moving forward or backward, or make an incision of wide area in a single movement.

As shown in FIG. 21, the protrusion part 60 of the distal tapered part 24, the protrusion part 60 of the straight tubular part 23, and the protrusion part 60 of the proximal tapered part 22 preferably extend continuously in the longitudinal axis direction x of the balloon body 20. The protrusion part 60 extending continuously in the longitudinal axis direction x of the balloon body 20 can improve the strength of the balloon 2 or easily further prevent overinflation of the balloon 2 when pressurized.

As shown in FIGS. 3 to 5, and 15 to 17, the balloon body 20 preferably has a wing forming portion 28 that forms the wing 29 in the deflated state, and the protrusion part 60 is preferably located outside the wing forming portion 28. When the protrusion part 60 is located outside the wing forming portion 28, the protrusion part 60 do not interfere with the folding of the wing 29, allowing the balloon 2 to be easily folded and reducing the outer diameter of the balloon 2 in the folded state. In a more preferable embodiment, a plurality of the wing 29 is formed in the deflated state as shown in FIG. 4 and FIG. 5, and the protrusion part 60 is preferably arranged between each wing 29. This allows the protrusion part 60 to be protected by the wing 29 when the balloon 2 is folded as shown in FIG. 15 and FIG. 16, and can prevent damage to the protrusion part 60 or prevent the protrusion part 60 from acting on the body cavity wall in unintended places when the balloon 2 is folded and inserted into the body cavity. By adjusting the length of the wing 29 in the radial direction y by adjusting the diameter of the balloon 2 or the number of the wing 29, the extent to which the wing 29 covers the protrusion part 60 in the distal tapered part 24 and the proximal tapered part 22 can be adjusted as shown in FIG. 16 and FIG. 17. In other words, when the wing 29 is short enough not to cover the protrusion part 60 in the distal tapered part 24 and the proximal tapered part 22 at a part near the position of 0% $D_0$ close to the straight tubular part 23, the protrusion part 60 can be exposed from the wing 29 in most of the distal tapered part 24 and the proximal tapered part 22, and this exposed protrusion part 60 can be used to incise the stenosis while moving the balloon 2 forward or backward. Alternatively, the wing 29 can be made long enough to cover the protrusion part 60 beyond the position of 50% of the distal tapered part 24 and the proximal tapered part 22, in which case the portion of the protrusion part 60 exposed from the wing 29 can be made smaller, and thus, reducing the action of the protrusion part 60 when the balloon 2 is moved forward or backward. Thus, by adjusting the extent to which the wing 29 covers the protrusion part 60, it is possible to accommodate application to a variety of lesions.

While FIGS. 4, 5, and 15 to 17 show the embodiment in which the number of the wing 29 is three, the number of the wing 29 is not particularly limited as long as the balloon 2 can be folded, and for example, the number of the wing 29 is preferably 2 or more, more preferably 3 or more, or may be 4 or more, or 5 or more. The lower limit of the number of the wing 29 in the above range can reduce the diameter of the balloon 2 while covering the protrusion part 60 when folded to improve insertion in the body cavity. The number of the wing 29 is preferably 10 or less, more preferably 8 or less, and even more preferably 6 or less. When the upper limit of the number of the wing 29 is within the above range, even the balloon 2 with a large diameter can be easily folded. By setting the number of the wing 29 in the above range, the size of the portion of the protrusion part 60 covered by the wing 29 in the distal tapered part 24 and the proximal tapered part 22 can be adjusted.

Materials forming the balloon body 20 include, for example, polyolefin-based resin such as polyethylene, polypropylene, ethylene-propylene copolymer; polyester-based resin such as polyethylene terephthalate and polyester elastomer; polyurethane-based resin such as polyurethane and polyurethane elastomer; polyphenylene sulfide-based resin; polyamide-based resin such as polyamide and polyamide elastomer; fluorine-based resin; silicone-based resin; and natural rubber such as latex rubber. Only one of these may be used, or two or more may be used in combination. Of these, polyamide-based resin, polyester-based resin, and polyurethane-based resin are preferably used. In particular, elastomer resin is preferably used from the viewpoint of thinning and flexibility of the balloon body 20. For example, among polyamide-based resins, nylon 12, nylon 11, and the like are suitable for the resin forming the balloon body 20, and more preferably nylon 12 because it is relatively easy to mold when blow molding. Polyamide elastomers such as polyether ester amide elastomer and polyamide ether elastomer are also preferred in terms of thinning and flexibility of the balloon body 20. Of these, polyether ester amide elastomer is preferred in terms of high yield strength and good dimensional stability of the balloon body 20.

The protrusion part 60 is preferably made of the same material as the balloon body 20. When the protrusion part 60 is made of the same material as the balloon body 20, the protrusion part 60 is less likely to damage the outer surface of the balloon body 20 while maintaining the flexibility of the balloon 2. The balloon body 20 and the protrusion part 60 are preferably integrally molded. This can prevent the protrusion part 60 from falling off from the balloon body 20.

Materials forming the shaft 3 include, for example, polyamide-based resin, polyester-based resin, polyurethane-based resin, polyolefin-based resin, fluorine-based resin, polyvinyl chloride-based resin, silicone-based resin, and natural rubber. Only one of these may be used, or two or more may be used in combination. Of these, the material forming the shaft 3 is preferably at least one of polyamide-based resin, polyolefin-based resin, and fluorine-based resin. This can improve surface slipperiness of the shaft 3 and improve the insertion of the balloon catheter 1 into the body cavity.

The balloon 2 and the shaft 3 may be joined by adhesive bonding, welding, or by attaching a ring-shaped member at the point where the end of the balloon 2 and the shaft 3 overlap to swage them. Of these, the balloon 2 and the shaft 3 are preferably joined by welding. By welding the balloon 2 and the shaft 3, the bond between the balloon 2 and the shaft 3 is difficult to be released even when the balloon 2 is repeatedly inflated and deflated, easily increasing the strength of the bond between the balloon 2 and the shaft 3.

As shown in FIG. 1, the balloon catheter 1 may be provided with a hub 4 at a proximal side of the shaft 3, and the hub 4 may be provided with a fluid inlet 7 that is connected to the flow channel of the fluid supplied to the interior of the balloon 2. In addition, the hub 4 preferably has a guidewire insertion port 5 that is connected to the guidewire insertion channel. The balloon catheter 1 having the hub 4 provided with the fluid inlet 7 and the guidewire insertion port 5 can facilitate the operation of supplying fluid inside the balloon 2 to inflate and deflate the balloon 2 and delivering the balloon catheter 1 to a lesion site along a guidewire. The balloon 2 in accordance with embodiments of the present invention is applicable not only the so-called over-the-wire balloon catheter in which the guidewire is inserted over the distal to the proximal side of the shaft 3 as shown in FIG. 1, but also applicable to a so-called rapid exchange balloon catheter in which the guidewire is inserted from the distal side to the midway of the proximal side of the shaft.

The shaft 3 and the hub 4 may be joined by, for example, adhesive bonding or welding. Of these, the shaft 3 and the hub 4 are preferably joined by adhesive bonding. The adhesive bonding of the shaft 3 and the hub 4 can increase the bonding strength of the shaft 3 and the hub 4 to increase durability of the balloon catheter 1 when the materials forming the shaft 3 and the hub 4 are different, for example, in a case where the shaft 3 is made of material having high flexibility and the hub 4 is made of material having high stiffness.

The present invention also provides a method for producing the balloon 2 for balloon catheter 1 in accordance with embodiments of the present invention. The method for producing the balloon 2 in accordance with embodiments of the present invention will be described referring to FIGS. 22 to 27. FIG. 22 is a perspective view of a parison before expansion in accordance with one embodiment of the present invention, showing a configuration having a lumen and a thick-walled portion. FIG. 23 is a cross-sectional view in the radial direction of a first tubular member and a second tubular member of a producing method in accordance with one embodiment of the present invention. FIG. 24 is a radial cross-sectional view in a process of placing the distal tapered part in the first tubular member or a process of placing the proximal tapered part in the second tubular member in the producing method in accordance with one embodiment of the present invention, showing a radial cross-sectional view of a part in which the proximal end of the distal tapered part or the distal end of the proximal tapered part is placed in the first tubular member or the second tubular member, respectively. FIG. 25 is a radial cross-sectional view of the first tubular member or the second tubular member shown in FIG. 24 at different position in the longitudinal axis direction, showing a radial cross-sectional view of a position at which a part where the tip part of the protrusion part of the distal tapered part is located on the first direction side in the circumferential direction of the balloon body with respect to the straight line $L_d$ is placed, or a part where the tip part of the protrusion part of the proximal tapered part is located on the first direction side in the circumferential direction of the balloon body with respect to the straight line $L_p$. FIG. 26 is a radial cross-sectional view of the first tubular member or the second tubular member shown in FIG. 24 at still different position in the longitudinal axis direction, showing a radial cross-sectional view of a position at which a part where the tip part of the protrusion part of the distal tapered part is located further on the first direction side in the circumferential direction of the balloon body with respect to the straight line $L_d$ is placed, or a part where the tip part of the protrusion part of the proximal tapered part is located further on the first direction side in the circumferential direction of the balloon body with respect to the straight line $L_p$. The dashed lines in FIGS. 24 to 26 represent the circumferential position of the tip part of the protrusion part at the proximal end of the distal tapered part or the circumferential position of the tip part of the protrusion part at the distal end of the proximal tapered part, which correspond to the base point of the straight line $L_d$ or $L_p$. FIG. 27 is a radial cross-sectional view of a third tubular member of the producing method in accordance with one embodiment of the present invention.

A method for producing the balloon 2 in accordance with an embodiment of the present invention has a process of preparing a first tubular member 310, a second tubular member 320, and a third tubular member 330, each of which has an inner space extending in a longitudinal axis direction; a process of preparing a balloon for a balloon catheter having the balloon body 20 having an outer surface and an inner surface, the balloon body 20 having a straight tubular part 23, the distal tapered part 24 located distal to the straight tubular part 23, and the proximal tapered part 22 located proximal to the straight tubular part 23, and the distal tapered part 24, the straight tubular part 23, and the proximal tapered part 22 having the protrusion part 60 that projects outwardly in the radial direction y from the outer surface of the balloon body 20 and extends in the longitudinal axis direction x of the balloon body 20; and a process of placing the distal tapered part 24 in the first tubular member 310, placing the proximal tapered part 22 in the second tubular member 320, and placing the straight tubular part 23 in the third tubular member 330 in the deflated state of the balloon; and the method satisfies at least one of the following (1) and (2):

(1) at least a part of the protrusion part 60 of the distal tapered part 24 is in contact with an inner surface of the first tubular member 310 in the placing process; and (2) at least a part of the protrusion part 60 of the proximal tapered part 22 is in contact with an inner surface of the second tubular member 320 in the placing process.

Placing so that a part of the protrusion part 60 of the distal tapered part 24 is in contact with the inner surface of the first tubular member 310 allows the protrusion part 60 to be moved in the circumferential direction z of the balloon body 20. As a result, the tip part 61 of the protrusion part 60 of the distal tapered part 24 can be placed to curve toward the first direction $C_1$ side or the second direction $C_2$ side in the circumferential direction z of the balloon body 20 in the deflated state.

Placing so that a part of the protrusion part 60 of the proximal tapered part 22 is in contact with the inner surface of the second tubular member 320 allows the protrusion part 60 to be moved in the circumferential direction z of the balloon body 20. As a result, the tip part 61 of the protrusion part 60 of the proximal tapered part 22 can be placed to curve toward the first direction $C_1$ side or the second direction $C_2$ side in the circumferential direction z of the balloon body 20 in the deflated state.

To move the tip part 61 of the protrusion part 60 of the distal tapered part 24 in the circumferential direction z of the balloon body 20 in the deflated state, the above process (1) can be performed: to move the tip part 61 of the protrusion part 60 of the proximal tapered part 22 in the circumferential direction z of the balloon body 20 in the deflated state, the above process (2) can be performed: to move the tip part 61 of the protrusion part 60 of both the distal tapered part 24 and the proximal tapered part 22 in the circumferential direction z of the balloon body 20 in the deflated state, both the above (1) and (2) can be performed.

In the process of preparing the balloon, for example, the balloon can be prepared by placing a tubular parison 200 made of a resin as shown in FIG. 22 in a mold having a groove, followed by biaxially stretch-blow molding. The protrusion part 60 can be formed, for example, by inserting the parison 200 into the inner cavity of the mold such that a thick-walled portion 220 of the parison 200 is inserted into the groove of the mold, and then expanding the parison 200 by introducing fluid into a lumen 210 of the parison 200. When the protrusion part 60 is not formed on the distal sleeve part 25 or the proximal sleeve part 21 or the inner protrusion part is formed, for example, the balloon 2 can be produced by pressing the thick-walled portion 220 of the parison 200 against the part of the mold other than the groove, and then expanding the parison 200 by introducing fluid into the lumen 210 of the parison 200. The materials forming the parison 200 can be referred to the description of the materials forming the balloon body 20.

The first tubular member 310 in the case where the above process (1) of the producing method in accordance with the present invention, as shown in FIG. 23, has an inner space extending in the longitudinal direction x, and the cross-sectional shape in the radial direction y of the space is preferably different in the longitudinal direction x. In other words, the shape of the above-described space is different depending on the distance at which the tip part 61 of the protrusion part 60 of the distal tapered part 24 is moved in the circumferential direction z of the balloon body 20 in the deflated state. This allows the position where the inner surface of the first tubular member 310 and at least a part of the protrusion part 60 of the distal tapered part 24 is in contact with each other to be changed, and the distance at which the tip part 60 of the protrusion part 60 of the distal tapered part 24 is moved in the circumferential direction z of the balloon body 20 can be controlled while preventing the tip part 61 of the protrusion part 60 of the distal tapered part 24 from moving in the radial direction y of the balloon body 20 in the deflated state.

Examples of the shape of the space of the first tubular member 310 in a cross section in the radial direction y are described. The space of the first tubular member 310 at which the distal and proximal ends of the distal tapered part 24, i.e., at which the tip part 61 of the protrusion part 60 of the distal tapered part 24 at the base end and tip end of the straight line $L_d$, preferably has a shape that does not come into contact with the protrusion part 60, and for example, the space of the first tubular member 310 at a position at which the proximal end of the distal tapered part 24 is placed may be the shape shown in FIG. 24. When the moving of the tip part 61 of the protrusion part 60 of the distal tapered part 24 in the radial direction y of the balloon body 20 is to be prevented, the space of the first tubular member 310 at a position at which the portion of the tip part 61 of the protrusion part 60 of the distal tapered part 24 is placed on the first direction $C_1$ side in the circumferential direction z of the balloon body 20 with respect to the straight line $L_d$ preferably has a shape that is partially in contact with the protrusion part 60 as shown in FIG. 25. The space of the first tubular member 310 at a position at which the portion of the tip part 61 of the protrusion part 60 of the distal tapered part 24 is placed further on the first direction $C_1$ side in the circumferential direction with respect to the straight line $L_d$ preferably has a shape that is partially in contact with the protrusion part 60 as shown in FIG. 26. Thus, the change in shape of the space, as exemplified in FIGS. 24 to 26, allows the distance at which the tip part 61 of the protrusion part 60 of the distal tapered part 24 is moved in the circumferential direction z of the balloon body 20 to be adjusted while preventing the tip part 61 of the protrusion part 60 of the distal tapered part 24 from moving in the radial direction y of the balloon body 20 in the deflated state. Alternatively, although not shown in the figures, adjusting the cross-sectional shape of the space in the radial direction y of the first tubular member 310 can bring the inner surface of the first tubular member 310 into contact with a part of the protrusion part 60 while allowing the tip part 61 of the protrusion part 60 to move in the radial direction y, and thus, the tip part 61 of the protrusion part 60 can be moved in the circumferential direction z of the balloon body 20 allowing movement in the radial direction y, and the distance of movement in the circumferential direction z along the longitudinal direction x can be adjusted. The shape of the space of the first tubular member 310 is not limited by the examples shown in FIGS. 24 to 26, and may be any shape as long as the distance at which the tip part 61 of the protrusion part 60 of the distal tapered part 24 is moved in the circumferential direction z of the balloon body 20 while preventing or allowing the movement in the radial direction y in the deflated state can be adjusted.

The cross-sectional shape in the radial direction y of the first tubular member 310 and the second tubular member 320 preferably varies continuously in the longitudinal axis direction x. This allows the tip part 61 of the protrusion part 60 of the distal tapered part 24 and the tip part 61 of the protrusion part 60 of the proximal tapered part 22 to be moved in the circumferential direction z of the balloon body 20 continuously in the longitudinal direction x in the deflated state.

The third tubular member 330 has an inner space extending in the longitudinal direction x. The shape of the space of the third tubular member 330 in a cross section in the radial direction y may be the same as or different from the shape of the space of the first tubular member 310 at the position where the proximal end of the distal tapered part 24 is placed as shown in FIG. 27, and the area of the space of the third tubular member 330 in a cross section in the radial direction y is preferably larger than the area of the space of the first tubular member 310. This can prevent the protrusion part 60 of the straight tubular part 23, which is placed in the space of the third tubular member 330, from contacting the inner surface of the third tubular member 330, so that the inner surface of the third tubular member 330 does not interfere with the protrusion part 60 of the straight tubular part 23.

In the case where the process (2) is also performed in addition to the above-described process (1), the second tubular member 320 preferably has the same configuration as the above-described first tubular member 310. That is, the shape of the space of the second tubular member 320 in a cross section in the radial direction y at the position where the distal end of the proximal tapered part 22 is placed may be the shape as shown in FIG. 24, the shape of the second tubular member 320 at the position where a part in which the tip part 61 of the protrusion part 60 of the proximal tapered part 22 is located on the first direction $C_1$ side in the circumferential direction with respect to the straight line $L_d$ is placed may be the shape as shown in FIG. 25, and the shape of the second tubular member 320 at the position where a part in which the tip part 61 of the protrusion part 60 of the proximal tapered part 22 is located further on the first direction $C_1$ side in the circumferential direction with respect to the straight line $L_d$ is placed may be the shape as shown in FIG. 26. Similar to the first tubular member 310, the shape of the space of the second tubular member 320 in a cross section in the radial direction y is not limited to these examples. The second tubular member 320 having the above-described configuration can change the position where the inner surface of the second tubular member 320 and a part of the protrusion part 60 of the proximal tapered part 22 are in contact with each other, and can adjust the distance at which the tip part 61 of the protrusion part 60 of the proximal tapered part 22 is moved in the circumferential direction z of the balloon body 20 while preventing or allowing the movement in the radial direction y of the balloon body 20 in the deflated state.

In the case where only the above process (1) is performed and the process (2) is not performed, the second tubular member 320 preferably has the same configuration as the above-described third tubular member 330. This can prevent the protrusion part 60 of the proximal tapered part 22, which is placed in the space of the second tubular member 320, from contacting the inner surface of the second tubular member 320, so that inner surface of the second tubular member 320 does not interfere with the protrusion part 60 of the proximal tapered part 22.

In the case where only the above process (2) is performed and the process (1) is not performed, the first tubular member 310 preferably has the same configuration as the above-described third tubular member 330. This can prevent the protrusion part 60 of the distal tapered part 24, which is placed in the space of the first tubular member 310, from contacting the inner surface of the first tubular member 310, so that the inner surface of the first tubular member 310 does not interfere with the protrusion part 60 of the distal tapered part 24.

The length of the first tubular member 310 in the longitudinal direction x, the length of the second tubular member 320 in the longitudinal direction x, and the length of the third tubular member 330 in the longitudinal direction x are preferably almost the same as the length of the distal tapered part 24 in the longitudinal direction x, the length of the proximal tapered part 22 in the longitudinal direction x, and the length of the straight tubular part 23 in the longitudinal direction x, respectively.

In the above-described placing process, the first tubular member 310, the third tubular member 330, and the second tubular member 320 are preferably lined up in this order in the longitudinal direction x so that each center of the space in the cross section of the radial direction y is coincident, and the balloon 2 is preferably inserted into the space from the second tubular member 320 side. This allows the distal tapered part 24 to be placed in the first tubular member 310, the straight tubular part 23 to be placed in the third tubular member 330, and the proximal tapered part 22 to be placed in the second tubular member 320.

By performing the above-described placing process to determine the placement of the tip part 61 of the protrusion part 60, the placement of the tip part 61 of the protrusion part 60 in the distal tapered part 24 and/or the proximal tapered part 22 can be deformed. Subsequently, the balloon 2 can be folded by hand or using various folding machines. When the protrusion part 60 is disposed outside the wing forming portion 28, the balloon 2 is preferably folded so that the wing 29 covers the protrusion part 60. By folding the balloon 2 so as not to disrupt the deformed arrangement of the tip part 61 of the protrusion part 60, it is possible to obtain the balloon 2 in which the tip part 61 of the protrusion part 60 is curved in the circumferential direction z of the balloon body 20 in the folded state.

Materials forming that make up the first tubular member 310, the second tubular member 320, and the third tubular member 330 include, for example, synthetic resins such as polycarbonate-based resin, polyacetal-based resin, and fluorine-based resin; and metals such as iron, copper, and stainless steel.

The present application is the National Phase of PCT International Application No. PCT/JP2021/038820, filed on Oct. 20, 2021, which claims priority based on Japanese Patent Application No. 2020-215754 filed on Dec. 24, 2020. All the contents described in Japanese Patent Application No. 2020-215754 filed on Dec. 24, 2020 are incorporated herein by reference.

DESCRIPTION OF REFERENCE SIGNS

1: balloon catheter
2: balloon
3: shaft
4: hub
5: guidewire insertion port
7: fluid inlet
20: balloon body
20C: central axis of balloon body
21: proximal sleeve part
22: proximal tapered part
23: straight tubular part
24: distal tapered part
25: distal sleeve part
28: wing forming portion
29: wing
31: outer tube
32: inner tube
60: protrusion part
61: tip part
200: parison
210: lumen of parison
220: thick-walled portion of parison
310: first tubular member
320: second tubular member
330: third tubular member
$L_d$: straight line connecting tip part at $D_0$ and tip part at $D_{100}$ of distal tapered part
$L_p$: straight line connecting tip part at $D_0$ and tip part at $D_{100}$ of proximal tapered part
$C_1$: first direction
$C_2$: second direction
$D_0$: position of 0%
$D_{20}$: position of 20%
$D_{40}$: position of 40%
$D_{60}$: position of 60%
$D_{70}$: position of 70%
$D_{90}$: position of 90%
$D_{100}$: position of 100%
$C_d$: imaginary curved surface obtained by rotating $L_d$ around central axis of balloon body
$C_p$: imaginary curved surface obtained by rotating $L_p$ around central axis of balloon body
x: longitudinal axis direction
y: radial direction
z: circumferential direction

The invention claimed is:

1. A balloon for a balloon catheter comprising:

a balloon body having an outer surface and an inner surface, wherein the balloon body has a straight tubular part, a distal tapered part located distal to the straight tubular part, and a proximal tapered part located proximal to the straight tubular part, the distal tapered part, the straight tubular part, and the proximal tapered part each have a protrusion part that projects outwardly in a radial direction from the outer surface of the balloon body and extends in a longitudinal axis direction of the balloon body, the protrusion part of each of the distal tapered part, the straight tubular part, and the proximal tapered part has a tip part in a cross section in the radial direction of the balloon body, the balloon is configured so that the tip part of the protrusion part of the distal tapered part, the tip part of the protrusion part of the straight tubular part, and the tip part of the protrusion part of the proximal tapered part are located at a same position in a circumferential direction of the balloon body in the inflated state of the balloon for the balloon catheter, and the balloon satisfies at least one of the following (1) or (2):

(1) in a deflated state of the balloon for the balloon catheter, the tip part of the protrusion part of the distal tapered part is located on a first direction side and not on a second direction side, or located on the second direction side and not on the first direction side, in the circumferential direction of the balloon body with respect to a straight line $L_d$ connecting the tip part at a proximal end of the distal tapered part and the tip part at a distal end of the distal tapered part; and a maximum value of a distance from the straight line La to the tip part of the protrusion part of the distal tapered part in the deflated state of the balloon is greater than a maximum value of a distance from the straight line $L_d$ to the tip part of the protrusion part of the distal tapered part in the inflated state of the balloon; or (2) in the deflated state of the balloon for the balloon catheter, the tip part of the protrusion part of the proximal tapered part is located on a first direction side and not on a second direction side, or located on the second direction side and not on the first direction side, in the circumferential direction of the balloon body with respect to a straight line $L_p$ connecting the tip part at a distal end of the proximal tapered part and the tip part at a proximal end of the proximal tapered part; and a maximum value of a distance from the straight line $L_p$ to the tip part of the protrusion part of the proximal tapered part in the deflated state of the balloon is greater than a maximum value of a distance from the straight line $L_p$ to the tip part of the protrusion part of the proximal tapered part in the inflated state of the balloon.

2. The balloon for the balloon catheter according to claim 1, wherein the balloon for the balloon catheter is folded in the deflated state of the balloon for the balloon catheter.

3. The balloon for the balloon catheter according to claim 1, wherein in the deflated state of the balloon for the balloon catheter, the proximal end of the distal tapered part and the distal end of the proximal tapered part are nearest to the straight tubular part and are defined as a position of 0%, and the distal end of the distal tapered part and the proximal end of the proximal tapered part are defined as a position of 100% in the longitudinal axis direction of the balloon body, and the balloon satisfies at least one of the following (1) or (2):

(1) the tip part of the protrusion part in an entire extent of a section from a position of 20% to a position of 70% of the distal tapered part is located on the first direction side or on the second direction side with respect to the straight line $L_d$, and the tip part of the protrusion part in a section from a position of 90% to the position of 100% of the distal tapered part is not located on either the first direction side or the second direction side with respect to the straight line $L_d$; or (2) the tip part of the protrusion part in an entire extent of a section from a position of 20% to a position of 70% of the proximal tapered part is located on the first direction side or on the second direction side with respect to the straight line $L_p$, and the tip part of the protrusion part in a section from a position of 90% to the position of 100% of the proximal tapered part is not located on either the first direction side or the second direction side with respect to the straight line $L_p$.

4. The balloon for the balloon catheter according to claim 3, wherein the balloon satisfies at least one of the following (1) or (2):

(1) a distance from the straight line $L_d$ to the tip part of the protrusion part at a position of 40% of the distal tapered part is 1.2 times or longer than a distance from the straight line $L_d$ to the tip part of the protrusion part at a position of 60% of the distal tapered part; or (2) a distance from the straight line $L_p$ to the tip part of the protrusion part at a position of 40% of the proximal tapered part is 1.2 times or longer than a distance from the straight line $L_p$ to the tip part of the protrusion part at a position of 60% of the proximal tapered part.

5. The balloon for the balloon catheter according to claim 1, wherein in the deflated state of the balloon for the balloon catheter, the proximal end of the distal tapered part and the distal end of the proximal tapered part are nearest to the straight tubular part and are defined as a position of 0%, and the distal end of the distal tapered part and the proximal end of the proximal tapered part are defined as a position of 100% in the longitudinal axis direction of the balloon body, and the balloon satisfies at least one of the following (1) or (2) in the deflated state of the balloon for the balloon catheter:

(1) the tip part of the protrusion part in an entire extent of a section from a position of 20% to a position of 70% of the distal tapered part is located inside or at a same position in the radial direction of the balloon body with respect to an imaginary curved surface obtained by rotating the straight line $L_d$ around a central axis of the balloon body; or (2) the tip part of the protrusion part in an entire extent of a section from a position of 20% to a position of 70% of the proximal tapered part is located inside or at a same position in the radial direction of the balloon body with respect to an imaginary curved surface obtained by rotating the straight line $L_p$ around a central axis of the balloon body.

6. The balloon for the balloon catheter according to claim 1, wherein the balloon body has a wing forming portion that forms a wing in the deflated state, and the protrusion part is located outside the wing forming portion.

7. The balloon for the balloon catheter according to claim 1, wherein the protrusion part of the distal tapered part, the protrusion part of the straight tubular part, and the protrusion part of the proximal tapered part extend continuously in the longitudinal axis direction of the balloon body.

8. The balloon for the balloon catheter according to claim 1, wherein the protrusion part is composed of a same material as the balloon body.

9. A method for producing the balloon for the balloon catheter according to claim 1, comprising:

arranging a first tubular member, a second tubular member, and a third tubular member, each of which has an inner space, so that each of the inner spaces of the first tubular member, the second tubular member, and the third tubular member extends in the longitudinal axis direction;

preparing the balloon for the balloon catheter having the balloon body having the outer surface and the inner surface, the balloon body having the straight tubular part, the distal tapered part located distal to the straight tubular part, and the proximal tapered part located proximal to the straight tubular part, and the distal tapered part, the straight tubular part, and the proximal tapered part each having the protrusion part that projects outwardly in the radial direction from the outer surface of the balloon body and extends in the longitudinal axis direction of the balloon body; and placing the distal tapered part in the first tubular member, placing the proximal tapered part in the second tubular member, and placing the straight tubular part in the third tubular member in the deflated state of the balloon for the balloon catheter, so that the method satisfies at least one of the following (1) or (2):

(1) at least a part of the protrusion part of the distal tapered part is in contact with an inner surface of the first tubular member in the step of placing the distal tapered part; or (2) at least a part of the protrusion part of the proximal tapered part is in contact with an inner surface of the second tubular member in the step of placing the proximal tapered part.

* * * * *